(12) United States Patent
Burman et al.

(10) Patent No.: US 8,927,023 B2
(45) Date of Patent: Jan. 6, 2015

(54) BIOCOMPATIBLE, NON-BIODEGRADABLE, NON-TOXIC POLYMER USEFUL FOR NANOPARTICLE PHARMACEUTICAL COMPOSITIONS

(71) Applicant: Fresenius Kabi Oncology Limited, Gurgaon, Haryana (IN)

(72) Inventors: Anand C. Burman, Ghaziabad (IN); Rama Mukherjee, Ghaziabad (IN); Dhiraj Khattar, Ghaziabad (IN); Sanjoy Mullick, Ghaziabad (IN); Manu Jaggi, Ghaziabad (IN); Manoj Kumar Singh, Ghaziabad (IN); Mukesh Kumar, Ghaziabad (IN); Deepak Prusthy, Ghaziabad (IN); Pawan Kumar Gupta, Ghaziabad (IN); Rajendran Praveen, Ghaziabad (IN); Shobhit Singh, Ghaziabad (IN)

(73) Assignee: Fresenius Kabi Oncology Limited (IN)

( * ) Notice: Subject to any disclaimer, the term of this patent is extended or adjusted under 35 U.S.C. 154(b) by 0 days.

(21) Appl. No.: 13/633,638

(22) Filed: Oct. 2, 2012

(65) Prior Publication Data
US 2013/0274211 A1 Oct. 17, 2013

Related U.S. Application Data

(62) Division of application No. 12/159,310, filed as application No. PCT/IN2006/000504 on Dec. 26, 2006, now Pat. No. 8,338,562.

(30) Foreign Application Priority Data

Dec. 28, 2005 (IN) ........................... 1190/KOL/2005

(51) Int. Cl.
| | | |
|---|---|---|
| *A61K 47/30* | (2006.01) | |
| *A61K 47/32* | (2006.01) | |
| *C08F 220/56* | (2006.01) | |
| *C08F 222/12* | (2006.01) | |
| *C08F 226/10* | (2006.01) | |
| *C08F 222/38* | (2006.01) | |

(52) U.S. Cl.
CPC .............. *A61K 47/32* (2013.01); *C08F 220/56* (2013.01); *C08F 222/12* (2013.01); *C08F 226/10* (2013.01); *C08F 222/385* (2013.01)
USPC ........... 424/489; 424/486; 424/487; 424/501; 526/264; 526/271; 526/303.1; 526/318.3; 526/319; 526/328.5; 526/332

(58) Field of Classification Search
CPC .. C08F 220/56; C08F 226/10; C08F 2810/20; B01D 67/0088; B01D 67/0093; B01D 69/02; B01D 71/34
USPC .......... 424/489, 486, 487, 501; 526/264, 271, 526/303.1, 318.3, 328.5, 319, 332
See application file for complete search history.

(56) References Cited

U.S. PATENT DOCUMENTS

| | | | | | |
|---|---|---|---|---|---|
| 5,830,964 | A | * | 11/1998 | Liu et al. ........................ | 526/264 |
| 6,322,817 | B1 | * | 11/2001 | Maitra et al. ................... | 424/489 |
| 6,617,420 | B2 | | 9/2003 | Kuriyama et al. | |
| 8,313,777 | B2 | * | 11/2012 | Maitra et al. ................... | 424/501 |
| 2009/0318661 | A1 | | 12/2009 | Burman et al. | |

OTHER PUBLICATIONS

"U.S. Appl. No. 12/159,310, Response filed May 29, 2012 to Non Final Office Action mailed Feb. 28, 2012", 17 pgs.
"U.S. Appl. No. 12/159,310, Advisory Action mailed Dec. 16, 2011", 3 pgs.
"U.S. Appl. No. 12/159,310, Final Office Action mailed Sep. 14, 2011", 8 pgs.
"U.S. Appl. No. 12/159,310, Non Final Office Action mailed Feb. 28, 2012", 13 pgs.
"U.S. Appl. No. 12/159,310, Non Final Office Action mailed Mar. 28, 2011", 12 pgs.
"U.S. Appl. No. 12/159,310, Notice of Allowance mailed Aug. 16, 2012", 8 pgs.
"U.S. Appl. No. 12/159,310, Preliminary Amendment filed Jun. 26, 2008", 9 pgs.
"U.S. Appl. No. 12/159,310, Response filed Jun. 21, 2011 to Non Final Office Action mailed Mar. 28, 2011", 13 pgs.
"U.S. Appl. No. 12/159,310, Response filed Nov. 14, 2011 to Final Office Action mailed Sep. 14, 2011", 16 pgs.
"Application Serial No. 2846.001 US1, Response filed Jan. 13, 2012 to Final Office Action mailed Sep. 14, 2011", 15 pgs.

* cited by examiner

Primary Examiner — Gregory Listvoyb
(74) Attorney, Agent, or Firm — Schwegman Lundberg & Woessner, P.A.

(57) ABSTRACT

The invention relates to a biocompatible, non-biodegradable, and non-toxic polymer of formula (I), comprising of three monomeric units, selected from 1-Vinylpyrrolidne (VP), N-Isopropylactylamide (NIPAM), and ester of Maleic anhydride and Polyethylene glycol (MPEG), cross-linked with a bi-functional vinyl derivative, of high purity and substantially free of respective toxic monomeric contaminants, and a process for preparation thereof. The invention further relates to nanoparticulate pharmaceutical compositions of poorly water-soluble drugs or compounds comprising the polymer of the invention, which are safe, less-toxic and convenient for bedside administration to patients in need thereof. Furthermore, the invention relates to a highly selective method for preparation of nanoparticulate pharmaceutical compositions of poorly water-soluble drugs or compounds.

17 Claims, 12 Drawing Sheets

```
CURRENT DATA PARAMETERS
NAME        H_QueJmay05
EXPND                 2
PADCMJ                1

F2 - ACQUISITION PARAMETERS
DATE-            500000
TIME-              18.23
INSTRAM         90 x 300
PACBHD       5 ms DUAL 13
PLLPROG              zg
TO                32768
SOLVENT            CDCl3
NS                   16
DS                    2
SAM           4706.098 Hz
FIBRES        0.143680 Hz
AG           3.4800117 sec
HG                   32
DH            106.200 usec
DF            114.29 usec
TE              300.0 K
O1          2.00000000 sec
P1             10.00 usec
OE            114.29 usec
SF01       300 1318902 MHz
NJC1                 1M
PL1              -6.00 dB F2 - PROCESSING PARAMETERS
S1                15384
SF         300 1300051 MHz
NON                  EM
SS0                   0
L8               0.00 Hz
?8                    0
PC                 1.00

IO NNA PLOT PARAMETERS
EX             20.00 cm
F1P           10.795 ppm
F1           3240.04 Hz
F2P            5.252 ppm
F2            375.70 Hz
PPMCM      0 50236 ppm/cm
HZCM      180.78716 Hz/cm
```

FIG. 1
CONTINUED

PHOTOGRAPH FROM ANIMAL INJECTED IV WITH DESTROSE SHOWING A DILATED SUBCUTANEOUS VEIN. THERE IS MINIMAL INFLAMMATION IN THE PERIVEINOUS AREA
VEIN LUMEN

THROMBUS    VEIN LUMEN

FIBRIN

VEIN LUMEN

BIOCOMPATIBLE, NON-BIODEGRADABLE, NON-TOXIC POLYMER USEFUL FOR NANOPARTICLE PHARMACEUTICAL COMPOSITIONS

RELATED APPLICATIONS

This application is a divisional application of U.S. patent application Ser. No. 12/159,310, filed on Oct. 29, 2008, which application is a U.S. National-Stage entry under 35 U.S.C. §371 based on International Application No. PCT/IN2006/000504, filed Dec. 26, 2006 and published in English as WO 2007/074476 on Jul. 5, 2007, which designates the United States of America, and claims priority to Indian Patent Application No. 1190/KOL/2005, filed Dec. 28, 2005, which applications and publication are incorporated herein by reference in their entirety.

FIELD OF THE INVENTION

The present invention provides a biocompatible and non-biodegradable polymer of high purity, substantially free of monomeric contaminants and a process for preparation thereof.

The present invention further provides pharmaceutical compositions of poorly water-soluble drugs or compounds in nanoparticulate form utilizing the said polymer of the invention.

Furthermore, the present invention relates to a highly selective method for preparation of pharmaceutical compositions of poorly water-soluble drugs or compounds in nanoparticulate form as well as a method of administration of the same to patients in need thereof.

The polymer of the present invention being non-toxic and safe, thereby render the nanoparticulate pharmaceutical compositions of poorly water-soluble drugs or compounds comprising the said polymer also less-toxic and safer for administration.

BACKGROUND OF THE INVENTION

Recent years have seen an ever-increasing interest in the application of novel materials in the medical and pharmaceutical fields, whether as prostheses or in medical devices designed for contact with biological environment of the living body. Of these materials, polymers, mainly synthetic polymers, are by far the most diverse classes that are found to impart considerable benefits to the patient health care.

The applications of polymers in the medical and pharmaceutical field are wide ranging. In the medical field, polymers are employed as implants or support materials such as artificial organs, vascular grafts, intraocular lenses, artificial joints, mammary prostheses, suture materials, extracorporeal therapeutics or other support materials such as those used in hemoperfusion, blood oxygenators, catheters, blood tubing, wound and burn covering materials, splints, contact lenses etc. In the pharmaceutical field, polymers have been particularly used in development of nanoparticle delivery systems and controlled-release delivery systems. Extensive studies are also being pursued to target drugs with delivery systems to the desired site. Further, polymers have found great utility in other applications as well, such as transdermal drug-delivery patches, micro spheres, bioprocesses such as enzyme and cell immobilization etc.

Amongst such applications, nanoparticluate drug delivery systems have been more extensively studied and nanometer-size drug carriers with hydrophilic surfaces, specially those comprising two spherical co-centric regions of polymeric micelles—a densely packed core of a hydrophobic material, which is responsible for entrapping a hydrophobic drug or compound and an outer shell made of hydrophilic material have been extensively studied. Such systems are found to evade recognition and uptake by the reticulo-endothelial systems (RES) and thus can circulate in the blood for a long time. Further, due to their extremely small size (a polymeric micelle usually consists of several hundred block copolymers and has a diameter of about 20 nm-50 nm), the particles extravasate at the pathological sites, such as solid tumors through passive targeting mechanism.

Polymers derive their range of properties attributable to their chemical and structural features. The polymer chains may essentially be linear, branched, or cross-linked to adjacent chains. Furthermore, these chains may be unordered, ordered or oriented in a single direction. These structural features combined with the chemical composition, lends a variety of properties to polymers, resulting in a variety of end-use applications. Further, these structural features combined with the chemical composition may impart or deprive the resultant polymer, biocompatibility and resistance to biodegradation by the host tissue environment. These factors also influence other properties such as solubility and methods of processing and moulding.

Moreover, when a polymer is injected into the mammals, it normally, slowly disappears from the site of administration, however, this disappearance occurs in response to a chemical reaction such as hydrolysis, which normally is a part of biotransformation process and the said polymer is metabolised and eliminated from the body. This, however, sometimes leads to unnecessary metabolites, which cause untoward effects on various biological systems. Therefore, polymers, which are inert in/to the environment of use, and are eliminated or extracted intact from the site of administration as well as serve essentially as a rate limiting barrier to transport and release of a drug from it, may be of prime importance based on the intended functions. Again, the biodegradability of a polymer depends on the mechanical and chemical properties of the polymer. A variety of natural, synthetic, and biosynthetic polymers are bio- and environmentally degradable. A polymer based on the C—C backbone tends to be non-biodegradable, whereas hetero atom-containing polymer backbones confer biodegradability. Non-biodegradability/biodegradability can therefore be engineered into polymers by the judicious deletion/addition of chemical linkages such as anhydride, ester, or amide bonds, among others Common examples of non-biodegradable polymer materials include polyethylene vinyl acetate, polydimethyl siloxane, polyether urethane, ethyl cellulose, cellulose acetate, polyethylene and polyvinyl chloride.

There is a welter of reports available on the attempts made over the last few decades or so on development of nanoparticulate delivery systems for a large variety of drugs utilizing polymers. To name a few, these include the disclosures of:
i) Sakurai et al in U.S. Pat. No. 5,412,072, wherein a complex comprising a drug covalently bonded to a polymer composed of hydrophilic and hydrophobic fragments is found to render the said complex water soluble and thereby suitable for administration. The drugs utilized therein are in general less water soluble or insoluble compounds and the drug-polymer complex is reported to form polymeric micelles in aqueous solutions and becomes water-soluble high molecular polymerized drugs, useful and suitable for administration.
ii) Yokoyama et al in U.S. Pat. No. 5,449,513, wherein they report a polymeric micelle, which unlike that disclosed by Sakurai et al in U.S. Pat. No. 5,412,072 is not a complex wherein a drug is covalently bonded to a polymer, but rather one wherein the drug is entrapped within the polymer. The drugs utilized for entrapment are hydrophobic in nature. The polymeric micelle is in turn prepared by entrapment of hydrophobic drugs inside the polymeric shell through conventional methods such as ultra sonication, followed by purification of the micelles thus obtained through dialysis.

iii) Desai et al in U.S. Pat. No. 5,439,686; U.S. Pat. No. 5,362,478; U.S. Pat. No. 5,916,596; U.S. Pat. No. 6,096,331; U.S. Pat. No. 6,537,579 and U.S. Pat. No. 6,749,868, wherein polymeric micelle of substantially water-insoluble compounds are prepared. The water-insoluble compound is reported to be entrapped inside the polymeric shell to a significant extent and suitable for administration to a patient in need thereof either in a soluble or suspended form.

The polymers utilized by Sakurai et al in U.S. Pat. No. 5,412,072 are in general those comprising a hydrophilic segment selected from polyethylene glycol, polysaccharides, polyacrylamide etc and a hydrophobic segment selected from polyaspartic acid, polyglutamic acid, polylysine etc.

The polymers utilized by Yokoyama et al in U.S. Pat. No. 5,449,513 are in general those comprising a hydrophilic segment selected from polyethylene oxide, polymalic acid, polyaspartic acid, polyglutamic acid, polylysine, polysaccharide etc and a hydrophobic segment selected from poly(β-benzyl L-aspartate), poly(γ-benzyl L-glutamate), poly(β-substituted aspartate), poly(γ-substituted glutamate), poly(L-leucine), poly(L-valine), poly(L-phenylalanine), hydrophobic polyamino acids, polystyrene, polymethacrylate, polyacrylate, polymethacrylate amide, polyacrylate amide, polyamide, polyester, polyalkylene oxide and hydrophobic polyolefins.

The polymers utilized by Desai et al in U.S. Pat. No. 5,439,686; U.S. Pat. No. 5,362,478; U.S. Pat. No. 5,916,596; U.S. Pat. No. 6,096,331; U.S. Pat. No. 6,537,579 and U.S. Pat. No. 6,749,868 are in general those essentially bearing sulfhydryl groups or disulfide bonds within its structure e.g. Albumin (which contains 35 cysteine residues), Insulin (which contains 6 cysteine residues), Haemoglobin (which contains 6 cysteine residues per $\alpha_2\beta_2$ unit), Lysozyme (which contains 8 cysteine residues), Immunoglobulins, α-2-Macroglobulin, Vitronectin, Vitronectin, Fibrinogen etc. Such polymers are substantially cross-linked through formation of disulphide bonds. Such polymers include both synthetic and natural polymers, which as mentioned hereinbefore, bear sulfhydryl groups or disulfide bonds within their structure. The sulfhydryl groups or disulfide linkages are reported to either be pre-existing or obtained through suitable chemical modifications. The natural polymers are reported to be preferred and include albumin proteins, oligopeptides, polynucleic acids etc.

However, the disadvantage with the polymeric micelles disclosed by Sakurai et al, Yokoyama et al, and Desai et al are that they all utilize polymers, both synthetic and natural, which are biodegradable. It might be mentioned that biodegradable polymers, although, are capable of influencing the drug release pattern as well as the release kinetics of the loaded drug, however, are not particularly preferred in drug delivery systems because they:

a) Have low plasma life time due to their rapid capture by the mononuclear phagocyte system (MPS) cells;

b) Lack response to physiological changes;

c) Lack consistent drug release kinetics which may economically and therapeutically cause waste of the drugs and other adverse effects; and d) May cause increase of toxicity or immunogenicity since encapsulation of protein drugs involves organic solvents, which may cause protein denaturation.

Delivery systems wherein polymers, which are non-biodegradable, have been utilized and disclosed by:

i) Maitra et al in U.S. Pat. No. 5,874,111, wherein the drug is entrapped within the polymer resulting in a highly monodispersed polymeric hydrophilic nanoparticle being formed. The polymers utilized are those comprising of monomers like Vinylpyrrolidone (VP) or mixture of Vinylpyrrolidone and polyethyleneglycolfumarate (PEGF), etc.

ii) Maitra et al in U.S. Pat. No. 6,322,817, wherein the polymers utilized comprise of at least one type of an amphiphilic monomer selected from the group consisting of vinylpyrrolidone, acrylic acid, alkyl acrylates having a chain length of $C_3$ to $C_6$ functionalized polyethylene glycol of a molecular weight of 2000 to 6000, N-alkylacrylamide having a chain length of $C_3$ to $C_6$, and alkylcyanoacrylate having a chain length of $C_3$ to $C_6$. The drugs entrapped within the polymeric micelles are taxane derivatives, in particular Paclitaxel.

iii) Lowe et al in US 2005/0169882, wherein the polymers utilized comprise of a smart segment (which is non-biodegradable) and a biodegradable segment. More specifically, the smart, non-biodegradable segment comprises of poly (N-isopropylacrylamide), poly(N-alkylacrylamide), poly (N-n-propylacrylamide), poly(N-isopropylmethacrylamide), poly(ethylene oxide)-poly(propylene oxide)-poly (ethylene oxide), elastin-like polypeptides, or a derivative thereof and the biodegradable segment comprises of polysaccharide, dextran, polyester, polylactide, poly(L-lactic acid), poly(D,L-lactic acid), poly(lactide-co-glycolides), biotinylated poly(ethylene glycol-block-lactic acid) etc.

In the case of polymers disclosed in U.S. Pat. No. 5,874,111, it might be noted that such polymers are prepared through polymerization of respective monomers and the polymeric material thus obtained is purified and isolated from an aqueous medium containing the same through a method of dialysis.

In the case of polymers disclosed in U.S. Pat. No. 6,322,817 also, the polymers are prepared through polymerization of respective monomers and is purified and isolated from an aqueous medium through a method of dialysis.

Similarly, the polymers disclosed by Lowe et al in US 2005/0169882 is also purified and isolated from an aqueous medium containing the same through a method of dialysis.

With regard to the compounds or drugs disclosed by Maitra et al in U.S. Pat. No. 5,874,111 for entrapment into polymers disclosed therein, they are primarily Antigens, Bovine serum etc. In the case of U.S. Pat. No. 6,322,817, the drugs for entrapment into polymers disclosed therein are primarily water-insoluble taxane derivatives, especially Paclitaxel, whereas Lowe et al in US 2005/0169882 disclose a wide host of drugs, which can be entrapped into the polymeric shell disclosed therein.

Further to the above, Burman et al in U.S. Pat. No. 6,365,191 teach a pharmaceutical composition comprising the polymer disclosed in U.S. Pat. No. 6,322,817, and more specifically a pharmaceutical composition of taxane derivatives, especially Paclitaxel. Herein, the said pharmaceutical composition is prepared by adding a solution of Paclitaxel in ethanol to an infusion vehicle comprising dextrose solution, to which has been added a solution of polymer in water containing an anionic surfactant and a buffering agent. Burman et al further claim that the pharmaceutical composition is stable for more than 12 hours without any precipitation of the drug from the perfusion fluid and that more than 90% (as analysed by HPLC) of the drug is entrapped within the polymeric micelle even after 24 hours of preparation of the perfusion fluid.

Even though, Burman et al in U.S. Pat. No. 6,365,191 claim that the pharmaceutical composition disclosed therein is in a nanoparticulate form, however, there is no mention in the specification as to the size of the claimed nanoparticulate form. The only mention about the particle size of the polymeric micelles containing Paclitaxel can be found in the disclosure by Maitra et al in U.S. Pat. No. 6,322,817, wherein the said nanoparticles containing Paclitaxel are reported to have a diameter in the range of 30-150 inn. Similarly, there is no mention about particle size of the polymeric micelles of the compositions disclosed by Lowe et al in US 2005/0169882.

It is important to note that the polymers disclosed in U.S. Pat. No. 5,874,111; U.S. Pat. No. 6,322,817; U.S. Pat. No. 6,365,191 and US 2005/0169882 are prepared from one or more monomers, which include Vinylpyrrolidone and N-Isopropylacrylamide. It is further, important to note that Vinylpyrrolidone and N-Isopropylacrylamide are toxic compounds, whose presence in a pharmaceutical composition meant for human/animal consumption is not only frowned upon by Health Authorities worldover, but also comes under stringent quality adherence, with strict limits set by Pharmacopoeial Forums worldover. For instance, the level of monomeric Vinylpyrrolidone in the polymer, Polyvinylpyrrolidone, as well as any other polymer containing Vinylpyrrolidone as a monomer, as prescribed by US and European Pharmacopoeias should not exceed a limit of 0.001% (i.e. <10 ppm).

There is a grave danger that in the methods described in U.S. Pat. No. 5,874,111; U.S. Pat. No. 6,322,817; U.S. Pat. No. 6,365,191 and US 2005/0169882 for preparation and isolation of polymers utilizing Vinylpyrrolidone as one of the monomers, the said monomer i.e. Vinylpyrrolidone may be present in limits higher than 0.001% (i.e. >10 ppm).

There is an equally grave danger that pharmaceutical compositions containing such polymers, utilising Vinylpyrrolidone as one of the monomers may also contain Vinylpyrrolidone as a monomeric contaminant and that the said monomer i.e. Vinylpyrrolidone may also be present in limits higher than 0.001% (i.e. >10 ppm).

This could be true especially with regard to the pharmaceutical compositions disclosed in U.S. Pat. No. 6,322,817; U.S. Pat. No. 6,365,191 and US 2005/0169882.

It need not be overemphasised that any chemical reaction including a reaction for preparation of polymers is never complete in the sense that invariably one or more of the reactants are left over in the product. This would apply to polymerization reactions involving Vinylpyrrolidone as a monomer and depending on the molar or weight proportions of Vinylpyrrolidone utilized, there is every possibility that some amount of the Vinylpyrrolidone would remain as a contaminant in the polymeric products prepared thereof.

In connection with the above, the present inventors concerns were found true, wherein analysis of the polymer prepared by polymerization of three monomers, viz. Vinylpyrrolidone (VP), N-isopropylacrylamide (NIPAM) and Ester of Maleic anhydride and polyethylene glycol (MPEG) exactly as per the description given in Examples I, II and III of U.S. Pat. No. 6,322,817 were found to contain an amount of N-isopropylacrylamide (NIPAM) and Vinylpyrrolidone (VP) as summarized Table-I.

TABLE I

Amount of Residual Monomers In The Polymer Prepared As Per The Method Described In Examples I, II and III Of U.S. Pat. No. 6,322,817

| Monomer | % w/w Detected In The Polymer |
|---------|-------------------------------|
| NIPAM   | 0.066-0.076 (660-760 ppm)     |
| VP      | 0.008-0.011 (80-110 ppm)      |

It would be abundantly evident that the amount of Vinylpyrrolidone found in the polymer is at least more than eight times the toxic limit of 0.001% (i.e. 10 ppm), wherein the pharmaceutical composition containing such a polymer would be very unsafe and highly toxic for administration to humans or animals.

A need, if not imperative exists not only for a polymer substantially free of toxic monomers, such as N-isopropylacrylamide (NIPAM) and Vinylpyrrolidone (VP) but also for pharmaceutical compositions comprising a polymer, which are substantially free of toxic monomeric contaminants, such as N-isopropylacrylamide (NIPAM) and Vinylpyrrolidone (VP).

It might also be noted that the pharmaceutical compositions disclosed by Burman et al in U.S. Pat. No. 6,365,191 are reported to have a stability of only about 12 hrs or more with 90% or more of the drug entrapped within the polymeric micelle at the end of 24 hours. Further, the pharmaceutical compositions disclosed by Lowe et al in US 2005/0169882 are reported to have a loading of the biologically active substances of approximately 40% only, with a release of the biologically active substance between a few hours to up to several days.

A further need exists for pharmaceutical compositions, which have longer stability as well as higher drug loading, which moreover are safe and less-toxic.

The present invention is a step forward in advancement of not only providing a polymer, which is substantially free of toxic monomeric contaminants, but also providing a pharmaceutical composition comprising such a desired polymer, which is safe for human/animal administration and has longer stability.

OBJECTS OF THE INVENTION

An object of the present invention is to provide a biocompatible and non-biodegradable polymer of high purity, substantially free of monomeric contaminants.

Another object of the present invention is to provide a process for preparation of a biocompatible and non-biodegradable polymer of high purity, substantially free of Monomeric contaminants.

Yet another object of the present invention is to provide pharmaceutical compositions of poorly water-soluble drugs or compounds in nanoparticulate form comprising biocompatible and non-biodegradable polymers, of high purity and substantially free of monomeric contaminants.

A further object of the present invention is to provide a method for preparation of pharmaceutical compositions of poorly water-soluble drugs or compounds in nanoparticulate form utilizing biocompatible and non-biodegradable polymers, of high purity and substantially free of monomeric contaminants.

Yet further object of the present invention is to provide nanoparticulate pharmaceutical compositions of poorly water-soluble drugs or compounds comprising biocompatible and non-biodegradable polymers of high purity and free of monomeric contaminants, which are safe and less-toxic.

Another objective of the present invention is to provide a highly selective method for preparation of pharmaceutical compositions in nanoparticulate form comprising poorly water soluble drugs or compounds and a biocompatible and non-biodegradable polymer of high purity and free of monomeric contaminants.

Yet another object of the present invention is to provide a method of administration of the nanoparticulate pharmaceutical compositions comprising a biocompatible and non-biodegradable polymer of highly purity and substantially free of monomeric contaminants to patients in need thereof.

A further object of the present invention is to provide nanoparticulate pharmaceutical compositions comprising a biocompatible and non-biodegradable polymer of high purity and free of monomeric contaminants, which are stable for longer periods of time.

ABBREVIATIONS USED IN THE INVENTION

VP=Vinylpyrrolidone or 1-Vinylpyrrolidin-2-one
NIPAM=N-Isopropylacrylamide
MPEG=Ester of Maleic anhydride and Polyethylene glycol
MBA=N,N'-methylenebisacrylamide
TMED=Tetramethylethylenediamine
APS=Ammonium persulphate
LCST=Lower Critical Solution Temperature
DSC=Differential Scanning calorimetry
TGA=Thermogravimetric Analysis
CMC=Critical Micelle Concentration

SUMMARY OF THE INVENTION

Figure 1:
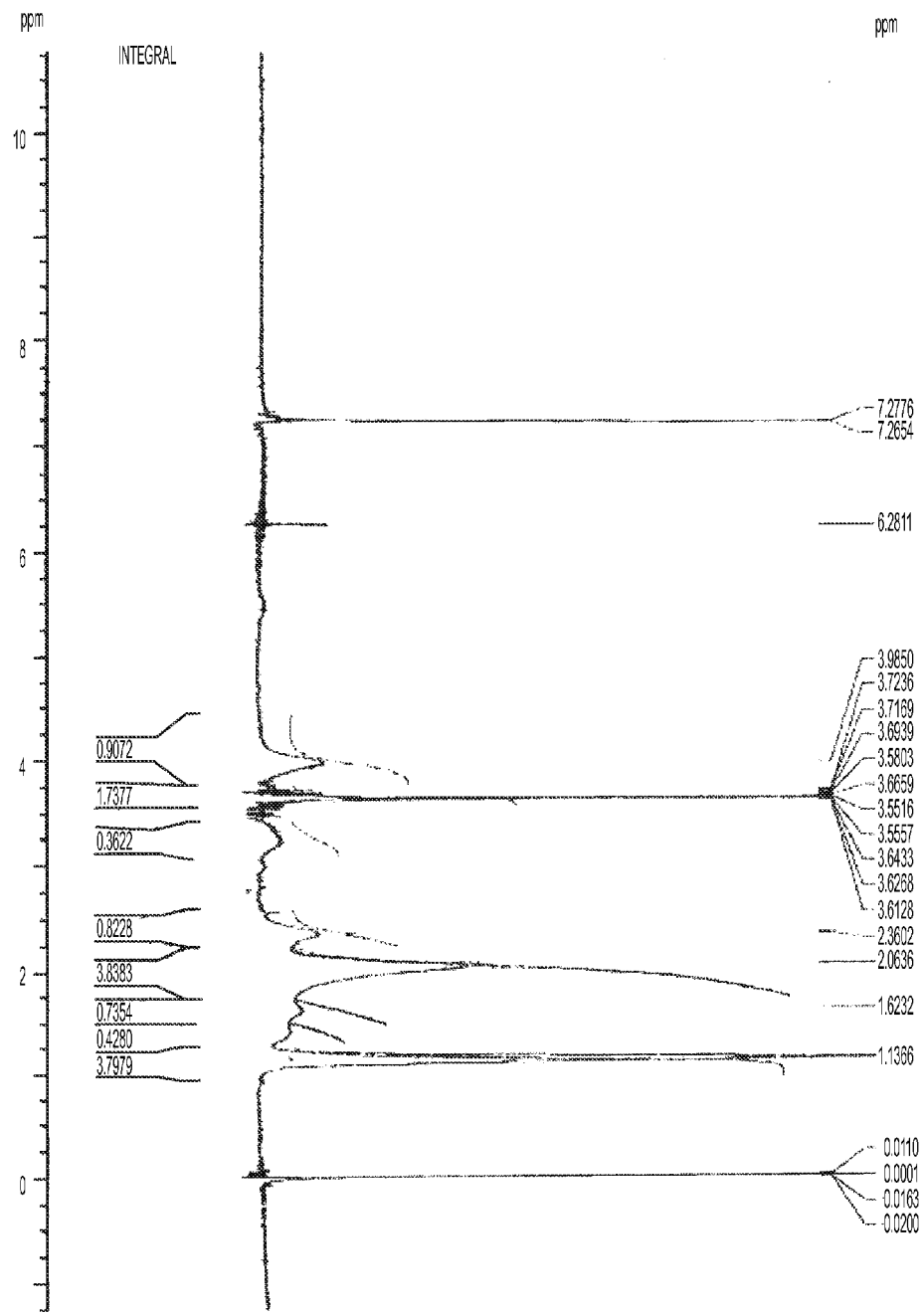
FIG. 1: The $^1$H-NMR Spectrum of the Polymer of the present invention.

In their endeavours, the present inventors have found that all the objectives set forth could be achieved, which moreover overcomes most, if not all the limitations of the prior art.

In the first place, the present inventors have found that a polymer comprising a monomeric unit of both NIPAM and VP could be obtained, wherein the amount of the respective individual monomeric contaminants in the polymer thus obtained is below the toxic limits prescribed.

In particular, the present inventors have found that a polymer comprising NIPAM, VP and MPEG as monomeric units could be obtained, which is substantially free of monomeric contaminants of toxic NIPAM and VP. Specifically, the present inventors have found that such a polymer could be obtained in high purity containing the said NIPAM and VP contaminants in levels much lower than 0.001% w/w.

The polymer having the desired characteristics could be obtained through a highly selective method, comprising subjecting an aqueous solution containing the polymer obtained by polymerization of NIPAM, VP and MPEG to a step of diafiltration or ultrafiltration, unlike the methods of dialysis, as taught in the prior art.

That the polymer obtained by the method of the present invention is superior to prior art methods, especially the method disclosed in U.S. Pat. No. 6,322,817, involving a step of dialysis could be best understood from a comparison of the residual monomers contained in the respective polymers, as summarized in Table-II.

TABLE II

A Comparison Of The Monomeric Contaminants Contained In The Polymer Obtained As Per The Process Disclosed in U.S. Pat. No. 6,322,817, Utilising Dialysis Vis-à-vis The Polymer Obtained As Per The Present Invention, Utilising Diafiltration

| Parameter | The Polymer Obtained As Per The Method Of U.S. Pat. No. 6,322,817 | The Polymer Obtained As Per The Method Of The Present Invention |
|---|---|---|
| Residual NIPAM | 0.066-0.076% w/w (660-760 ppm) | <0.001% w/w (<10 ppm) |
| Residual VP | 0.008-0.011% w/w (80-110 ppm) | <0.001% w/w (<10 ppm) |

It should be noted that dialysis is a process, which involves slow separation of smaller molecules from larger molecules or of dissolved substances from colloidal particles in a solution by selective diffusion through a semipermeable membrane. In a typical dialysis method, the polymer solution for purification is contained within a semipermeable membrane and the low-molecular weight solutes (monomers) are removed by placing a pure solvent, generally water outside the membrane. This solvent is changed periodically or continuously until the concentration of diffusible solutes (monomers like NIPAM and VP) in the solution containing the polymer is reduced.

Unlike the dialysis method, the diafiltration technique involves mechanical flow of fluid by a pump across the membrane, whereby the fluid is pumped tangentially (for this reason diafiltration is also known as Tangential Flow Filtration), along the surface of the membrane. An applied pressure forces a portion of the fluid to diffuse selectively through the membrane to the filtrate side. The retained polymeric components do not build up at the surface of the semipermeable membrane.

In contrast to the dialysis method, wherein the initial quantity or volume of the aqueous solution of the polymer taken up for purification remains as such/or same or gets diluted at the end or completion of the said operation, in the diafiltration method, on the other hand, since the aqueous solution of the polymer is swept along by tangential flow, concurrently results in concentration of the said solution containing the polymer, resulting in a more concentrated solution of the polymer. For example, when a solution containing, say 100 gm of the polymer in 5.0 Lts of water is subjected to dialysis and diafiltration respectively, at the end of the former method a solution containing 100 gm of the polymer in 4.5 to 5.5 Lts of water is obtained, whereas at the end of the latter method a reduction in or concentration of the initial volume results, generally to a tune of between one-fourth to one-sixth ($1/4^{th}$ to $1/6^{th}$) the initial volume, and at the end a solution of 100 gm of the polymer in about 0.8 to 1.3 Lts of water is obtained.

Further, as mentioned hereinbefore, in the dialysis method the solvent kept outside the membrane containing the solution of the polymer needs to be changed periodically or continuously manually, whereas in the diafiltration method no such manual operation of periodic or continuous change of any solvent is necessary. This renders the former tedious requiring manual supervision during its operation, whereas the latter method is fully automated and regulated and hence less tedious and convenient requiring no manual supervision during its operation.

Furthermore, by virtue of the diafiltration method being operable under a closed environment in comparison to the dialysis method, which operates under an open environment, any possibility of microbial contamination is Minimal or non-existent in the former method and therefore, would qualify as an operation under aseptic conditions, conforming to not only Good Manufacturing Practices but also conforming to Regulatory Guidelines worldover.

Further, by virtue of not only involving manual operation but also the inherent principle under which the dialysis method works, the time cycle for an unit operation is lengthy and generally takes about 24-36 hours. In comparison, the diafiltration method by virtue of the inherent principle under which it works requires a very short time cycle and usually takes less than one hour for completion. To say in other words, the diafiltration method is at least twenty five (25) times faster than the dialysis method and hence industrially more suited.

While, the dialysis method calls for a rather lengthy time cycle for operation and completion, another inherent disadvantage of the said method is that it allows only a small volume/quantity of a solution of the polymer to be purified. Such limitations do not rest with the diafiltration method and in general it allows a larger volume/quantity, say to a tune of at least 4 to 5 times of a solution to be purified. For example, if the dialysis method has a capacity for purifying a solution of 100 gm of the polymer in 5.0 Lts of water in one cycle, by the diafiltration method in one cycle between 400 to 500 gm of the polymer in 20.0 to 25.0 Lts of water can be purified. Needless to mention, the larger processing capacity of the diafiltration method is another advantage it offers in addition to the others already discussed hereinbefore i.e. faster operation time, automated and regulated operation, convenient and less tedious, concurrent concentration of or reduction in volume of the initial solution, conforming to Good Manufacturing Practices and Regulatory Guidelines, minimal or non-existent microbial contamination etc.

However, as mentioned and discussed hereinbefore, the most important advantage the diafiltration method has over the dialysis method is in the purity of the polymer obtained by the respective methods, with the former method producing the polymer, substantially free of monomeric contaminants and hence non-toxic and safe for human/animal consumption [Refer Table-II].

Last, but not the least, another inherent advantage of the diafiltration method is that if the polymer is required/necessitated to be isolated in solid form from the solution, through evaporation of the solvent, e.g. through lyophilization then by virtue of the said method resulting in a reduction in or concentration of the initial volume of the polymer solution, generally to a tune of about one fourth to one-sixth ($1/4^{th}$ to $1/6^{th}$) of the initial volume, the evaporation/lyophilization time cycle would also be drastically reduced. In the dialysis method, since no reduction in or concentration of the initial volume takes place, if the polymer is required/necessitated to be isolated in solid form from the solution, the evaporation/lyophilization time cycle would be much higher.

In short, the diafiltration method in comparison to the dialysis method is easily scaleable for large manufacturing, conforming to Good Manufacturing Practices, and hence industrially more viable and friendly.

The essential differences between the diafiltration and the dialysis methods in are summarised in Table-III, for quick reference.

While, to some extent the diafiltration or ultrafiltration technique is applied to various purifications, however, their application in the field of polymers is hitherto not reported and forms the novel and inventive aspect of the present invention.

Figure 6:
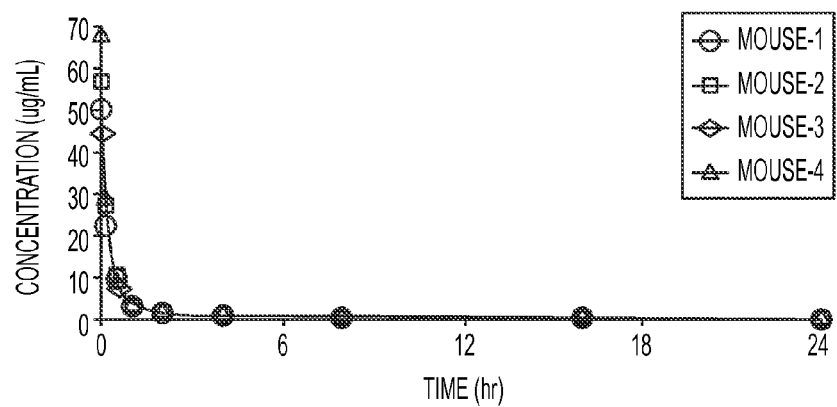
FIG. 6: The Pharmacokinetic Blood Profile of the [$^{14}$C]-labelled Polymer of the present invention.

Further, the present inventors have further characterized the polymer of high purity and substantially free from monomeric contaminants thus obtained, by various spectroscopic methods such as $^1$H-NMR, $^{13}$C-NMR and Fourier Transform Infrared (FT-IR) and found it to have the structure (I) as shown hereinbelow:

Furthermore, based on studies with Radio-labelled polymer in male Swiss albino mice, as would be evident from the details given in the later part of this Specification [refer Tables-VI and VII and FIG. 6], it was found that the polymer of the present invention is non-biodegradable and is rapidly eliminated from the body without being deposited and degraded in vital organs, suggesting the safety and utility of the polymer for human/animal use.

TABLE III

A Comparison Of The Dialysis And Diafiltration Methods Vis-à-vis Purification Of An Aqueous Solution Of The Polymer Of The Present Invention

| Parameter | Dialysis Method | Diafiltration Method |
|---|---|---|
| Batch Size | Limited and Hence a Constraint (e.g. 100 gm of Polymer in 5.0 Lts of water) | At least 4-5 times the Volume/Quantity can be Processed (e.g. 400 to 500 gm of Polymer in 20.0 to 25.0 Lts of water) |
| Processing Conditions | Open Environment | Closed Environment |
| Processing Time | Lengthy (24-36 Hours) | Shorter (<1 Hour) |

TABLE III-continued

A Comparison Of The Dialysis And Diafiltration Methods Vis-à-vis
Purification Of An Aqueous Solution Of The Polymer Of The Present Invention

| Parameter | Dialysis Method | Diafiltration Method |
|---|---|---|
| Operation and Convenience | Manual; Tedious; Less Convenient | Automated and Regulated; Less Tedious; Highly Convenient |
| Microbial Contamination | High Possibility | Minimal or Non-Existent |
| Reduction in/Concentration of Initial Volume of the Solution | None | About one-fourth to one-sixth ($1/4^{th}$ to $1/6^{th}$) |
| Lyophilization Time Cycle of The solution | Lengthy (90-110% of Initial Volume to be Lyophilized) | Shorter (only 15-25% of Initial Volume to be Lyophilized) |
| Monomeric Contamination | Very High | Below Pharmacopoeial and Toxic Limits |
| Scalability and Industrial Viability | Difficult; Less Viable | Easily Scaleable; Conforming to Good Manufacturing Practices; Highly Viable |

Further, based on extensive toxicity studies such as Localized Toxicity (Subcutaneous and Intravenous), Target Organs Dose Toxicity up to 800 mg/kg animal body weight, Six Months Cyclical Dose Toxicity etc., as would be evident from the details given in the later part of this Specification [refer FIGS. 7-10], it was found that the polymer of the present invention polymer is non-toxic, biocompatible and biologically safe for use in making pharmaceutical compositions meant for human/animal use and administration.

It was further found that the polymer of the present invention, which is of high purity and substantially free of monomeric contaminants and further being biocompatible, non-biodegradable, safe and non-toxic is particularly useful in preparation of pharmaceutical compositions, comprising the said polymer in nanoparticulate form along with pharmaceutically acceptable excipients, which in turn are safe and less-toxic for human/animal use and/or administration.

Especially, the biocompatible, non-biodegradable, safe and non-toxic polymer of the present invention was found to entrap completely or near-completely within its polymeric shell a host of poorly water-soluble drugs or compounds, wherein the said poorly water-soluble drugs or compounds are available in nanoparticulate form, in particle sizes of between 30-150 nm.

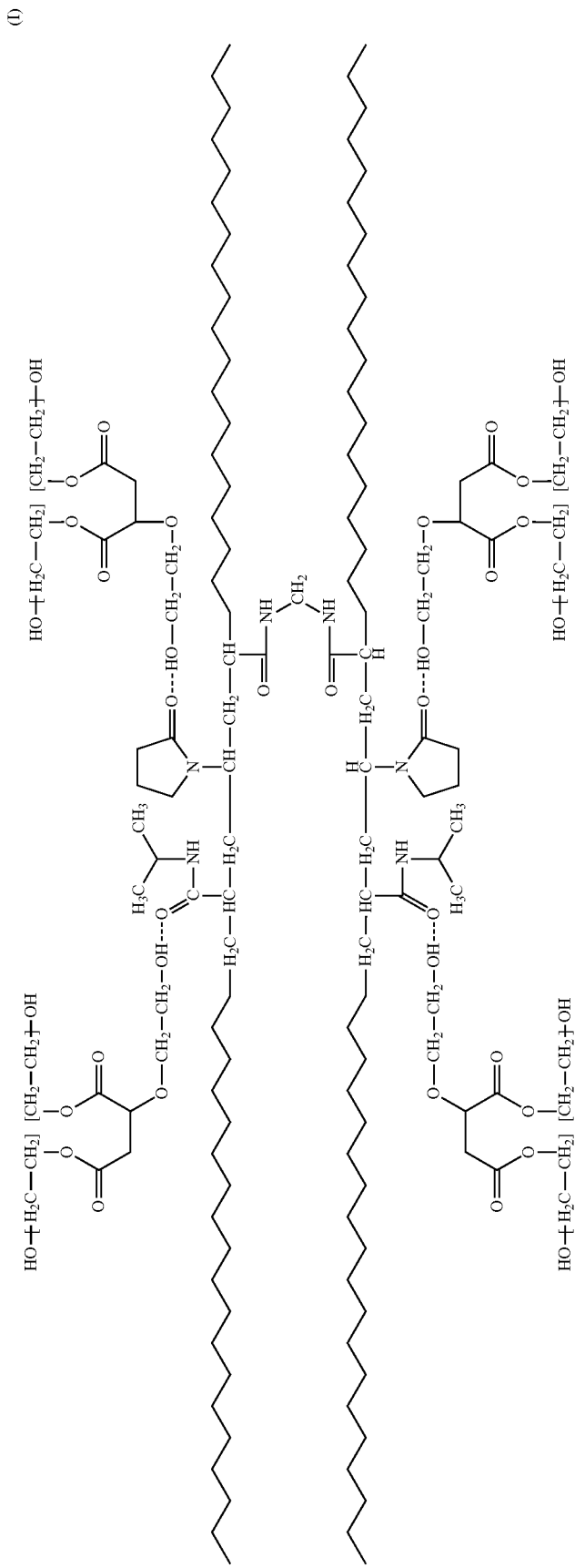

Structure of the Polymer of the Present Invention

In particular, it was found that the polymer of the present invention could be used to prepare a pharmaceutical composition in nanoparticulate forms, along with pharmaceutically acceptable excipients entrapping a host of poorly water-soluble drugs or compounds completely or near-completely within its polymeric shell. Such poorly water-soluble drugs or compounds are those having water solubility of less than 10 mg/ml. Examples of such poorly water-soluble drugs or compounds include, but are not limited to, anticancer agents, anti-inflammatory agents, anti-fungal agents, antiemetics, antihypertensive agents, sex hormones, steroids, antibiotics, immunomodulators, anaesthetics etc. Typical examples of anticancer agents that can be entrapped within the polymeric shell are Paclitaxel, Docetaxel, and other related taxane derivatives; Irinotecan, Topotecan, and other related Camptothecin derivatives; Doxorubicin, Daunomycin, and related Anthracycline derivatives; Cisplatin; Oxaliplatin; 5-Fluorouracil; Mitomycin; Methotrexate; Etoposide; Betulinic acid and its derivatives; and Wedelolactone and its derivatives. Typical examples of anti-inflammatory agents that can be entrapped within the polymeric shell include Indomethacin, Ibuprofen, Ketoprofen, Flubiprofen, Piroxicam, Tenoxicam, and Naproxen. Typical examples of anti-fungal agents that can be entrapped within the polymeric shell include Ketoconazole, and Amphotericin B. Typical examples of sex hormones that can be entrapped within the polymeric shell include Testosterone, Estrogen, Progesterone, and Estradiol. Typical examples of steroids that can be entrapped within the polymeric shell include Dexamethasone, Prednisolone, and Triamcinolone. Typical examples of antihypertensive agents that can be entrapped within the polymeric shell include Captopril, Ramipril, Terazosin, Minoxidil, and Parazosin. Typical examples of antiemetics that can be entrapped within the polymeric shell include Ondansetron and Granisetron. Typical examples of antibiotics that can be entrapped within the polymeric shell include Metronidazole, and Fusidic acid. Typical examples of immunomodulators that can be entrapped within the polymeric shell include Cyclosporine; and Biphenyl dimethyl dicarboxylic acid. Typical examples of anaesthetics that can be entrapped within the polymeric shell include Propofol, Alfaxalone, and Hexobarbital.

With regard to anticancer agents in particular, the polymer of the present invention was found capable of entrapping completely within its polymeric shell poorly-water soluble drugs or compounds like Paclitaxel, Docetaxel, Etoposide, and various Betulinic acid derivatives, such as those designated as MJ-1098, DRF-4012 and DRF-4015 having the following structures (II), (III), and (IV), which in turn are disclosed in U.S. Pat. No. 6,403,816 and our pending Indian Application No. 265/DEL/2005, filed on Feb. 9, 2005.

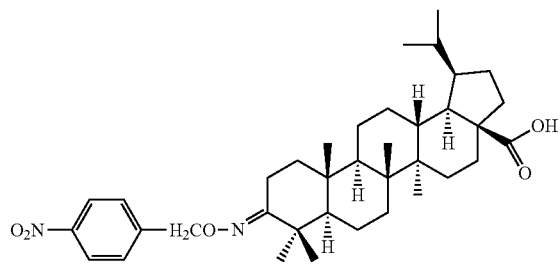

MJ-1098 (II), As Disclosed In U.S. Pat. No. 6,403,816

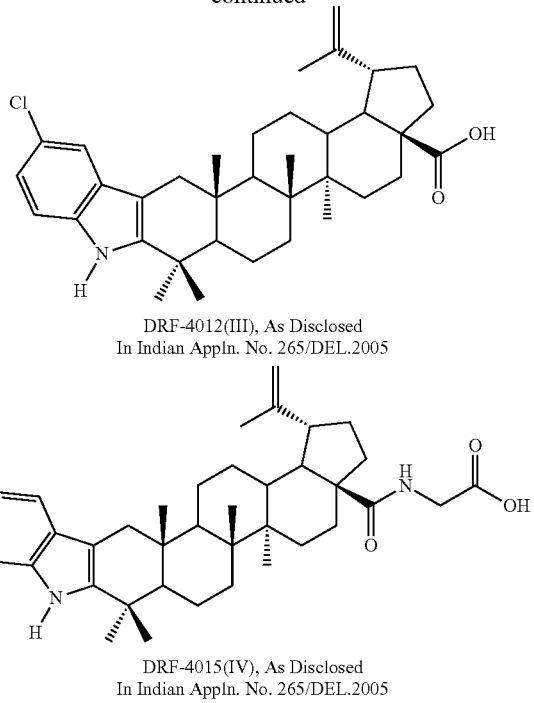

DRF-4012(III), As Disclosed
In Indian Appln. No. 265/DEL.2005

DRF-4015(IV), As Disclosed
In Indian Appln. No. 265/DEL.2005

The nanoparticulate pharmaceutical compositions of the poorly water-soluble drugs or compounds mentioned hereinbefore and specially the nanoparticulate pharmaceutical compositions of the poorly water-soluble drugs or compounds like Paclitaxel, Docetaxel and Etoposide and potent anticancer compounds like MJ-1098, DRF-4012 and DRF-4015, mentioned hereinbefore were found to have longer stability of greater than 24 hours in comparison to a nanoparticulate pharmaceutical composition of Paclitaxel prepared as per the method of Burman et al, disclosed in U.S. Pat. No. 6,365,191, which as claimed in the said patent has a stability of only 12 hours. By reference to the term "stability", it is to be construed to mean the period, counted in hours, wherein the poorly water-soluble drug or compound remains in solution in the pharmaceutical composition comprising the same, without any precipitation of the drug or compound from therein.

Further, in the nanoparticulate pharmaceutical compositions of the poorly water-soluble drugs or compounds, mentioned hereinbefore and specially in the nanoparticulate pharmaceutical compositions of the poorly water-soluble drugs or compounds like Paclitaxel, Docetaxel and Etoposide and potent anticancer compounds like MJ 1098, DRF 4012 and DRF 4015, mentioned hereinbefore, the said drugs or compounds were found to be entrapped within the polymeric micelle to an extent of greater than 95% even after 24 hours. In comparison, in a nanoparticulate pharmaceutical composition of Paclitaxel prepared as per the method of Burman et al, disclosed in U.S. Pat. No. 6,365,19, the drug was found to be entrapped within the polymeric micelle to an extent of only 90% even after 24 hours.

A comparison of the pharmaceutical compositions of poorly water-soluble drugs or compounds in nanoparticulate form, comprising the polymer of high purity and substantially free of monomeric contaminants of the present invention over the pharmaceutical composition of Paclitaxel, also in nanoparticulate form as disclosed in U.S. Pat. No. 6,365,191, would be evident from the comparison summarized in Table-IV.

TABLE IV

Comparison Of The Pharmaceutical Composition Of Poorly Water-Soluble Drugs Or Compounds Of The Present Invention Vis-à-vis The Pharmaceutical Composition Disclosed In U.S. Pat. No. 6,365,191

| Sr. No. | Details | Disclosure Contained In U.S. Pat. No. 6,365,191 | Present Invention |
|---|---|---|---|
| 1 | Poorly water-soluble Drugs or Compounds referred to | Taxane Derivatives, specially Paclitaxel | A host of Drugs and Compounds |
| 2 | The Polymer utilized in the Pharmaceutical Composition | Comprising of NIPAM, VP, and MPEG Monomeric Units | Comprising of NIPAM, VP, and MPEG Monomeric Units |
| 3 | Monomeric Contaminants present in the Polymer | NIPAM: 0.066-0.076% w/w VP: 0.008-0.011% w/w | NIPAM: <0.001% w/w VP: <0.001% w/w |
| 4 | Size of the Nanoparticles in the Pharmaceutical Composition | Not Specified | 30-150 nm |
| 4 | Stability | About 12 Hours | >24 Hours |
| 5 | Entrapment of the Drug within the Polymeric Micelle after 24 Hours | 90% | >95% |

In addition to the advantages of not only the polymer of high purity and substantially free of monomeric contaminants obtained as per the method of the present invention but also the advantages the pharmaceutical compositions of poorly water-soluble drugs or compounds, comprising the polymer of the present invention have over the polymers and pharmaceutical compositions of the prior art, as discussed in detail hereinbefore, the present inventors have further found a highly selective method for preparation of pharmaceutical compositions of poorly water-soluble drugs or compounds, wherein the said poorly water-soluble drug or compound, entrapped within the polymeric shell of the polymer utilized therein is produced in a nanoparticulate form of consistent size. This highly selective method forms another inventive aspect of the present invention.

In the first place, it might be noted that from the description contained in Examples 1-40 and that given under the heading "The Preferred Composition" and "Formulation for Infusion" in U.S. Pat. No. 6,365,191 of Burman et al, the pharmaceutical composition of Paclitaxel is apparently prepared first by dissolving the requisite amount of the polymer in a requisite amount of a diluting fluid (generally a 5% or 10% Dextrose solution), followed by addition of an anionic surfactant to obtain a clear solution, the pH of which is optionally adjusted with a buffering agent. To the resultant clear solution of the polymer and the anionic surfactant in the diluting fluid is then added an alcoholic solution of Paclitaxel to obtain varying drug concentration ranging from 0.1 to 10 mg/ml, which essentially is claimed to be the pharmaceutical composition in nanoparticulate form useful for administration.

As mentioned hereinbefore, while U.S. Pat. No. 6,365,191 is silent about the size of the nanoparticles thus obtained, it, however, was found to produce or result in inconsistent sizes of the nanoparticles in the hands of the present inventors in their attempts to prepare a pharmaceutical composition of Paclitaxel, as per the method described in Examples 1-40 and that given under the heading "The Preferred Composition" and "Formulation for Infusion" in U.S. Pat. No. 6,365,191 of Burman et al.

Against this background, the present inventors found that production of nanoparticles in consistent sizes was highly selective and depends largely on:

i) The rate at which an alcoholic solution of Paclitaxel is added to a solution of the polymer and other excipients in the diluting fluid;

ii) The volume of the alcoholic solution of Paclitaxel and the volume of the diluting fluid, to which the former is added;

iii) The internal diameter or bore size of the needle through which the alcoholic solution of Paclitaxel is added to a solution of the polymer and pharmaceutically acceptable excipients in the diluting fluid; and iv) The position of the container, which contains the diluting fluid and the polymer and pharmaceutically acceptable excipients at the time of addition of the alcoholic solution of Paclitaxel.

In particular, the present inventors have found that only through:

a) Addition of an alcoholic solution of Paclitaxel through a syringe to a solution of the polymer and other excipients in the diluting fluid within a specified period of time;

b) Utilization of a needle having an internal diameter of between 0.305 mm to 0.356 mm, for addition of a smaller volume of the alcoholic solution of Paclitaxel to the solution of the polymer and pharmaceutically acceptable excipients in the diluting fluid; or c) Utilization of a needle having an internal diameter of between 0.559 to 0.711 mm, for addition of a larger volume of the alcoholic solution of Paclitaxel to the solution of the polymer and pharmaceutically acceptable excipients in the diluting fluid;

d) Injection of an alcoholic solution of Paclitaxel to the solution of the polymer and other excipients in the diluting fluid, wherein the needle of the syringe through which the alcoholic solution of Paclitaxel is added shall remain dipped in the diluting fluid solution; and e) Optionally, keeping the container containing the said diluting fluid in an inverted position during injection of an alcoholic solution of Paclitaxel to the solution of the polymer and other excipients in the diluting fluid, production of nanoparticles of consistent particle sizes, with minimal or negligible size variation and consistent loading of the drug, within the polymeric shell could be achieved.

Further, only through the selective method it was found a longer stability of the pharmaceutical composition could be achieved.

It was further found that the highly selective method, mentioned hereinbefore is not limited to production of nanoparticles of Paclitaxel only, but also is equally effective in production of nanoparticles of consistent particle sizes of other poorly water-soluble drugs or compounds, especially Docetaxel, Etoposide, Betulinic acid, potent anticancer betulinic acid derivatives like MJ-1098 of formula (II), DRF-4012 of formula (III), DRF-4015 of formula (IV), referred to hereinbefore.

It was particularly found that if the addition time of a smaller volume, say of between 1 to 5 ml of the solution of the poorly water-soluble drug or compound to a solution (about 35 times the volume injected) of the polymer and other excipients in the diluting fluid, exceeds a time of 4 seconds, or if the internal diameter of the needle (through which the solution of the poorly water-soluble drug or compound is injected) is outside the range of 0.305 mm to 0.356 mm, then such an addition results in production of inconsistent particle sizes of the nanoparticles of the poorly water-soluble drugs or compounds as well as results in a pharmaceutical composition possessing poor stability, meaning whereby the solution does not remain clear for longer periods of time but becomes opalescent in shorter periods of time.

Similarly, it was particularly found that if the addition time of a larger volume, say of between 5 to 15 ml of the solution of the poorly water-soluble drug or compound to a solution (about 35 times the volume injected) of the polymer and other excipients in the diluting fluid, exceeds a time of 10 seconds, or if the internal diameter of the needle (through which the solution of the poorly water-soluble drug or compound is injected) is outside the range of 0.559 to 0.711 mm, then such an addition results in production of inconsistent particle sizes of the nanoparticles of the poorly water-soluble drugs or compounds as well as results in a pharmaceutical composition possessing poor stability, meaning whereby the solution does not remain clear for longer periods of time but becomes opalescent in shorter periods of time.

This could be exemplified with respect to pharmaceutical compositions of two poorly water-soluble anticancer drugs or compounds, viz. Paclitaxel and a Betulinic acid derivative, DRF-4012 of formula (III), wherein the effect of the time of addition of a solution of the said drugs and the internal diameters of the needles through which such solutions are added to the solution of the polymer and pharmaceutically acceptable excipients in the diluting fluid are summarized in Table-V.

The pharmaceutical composition of the present invention is conveniently presented as a two vial kit:

a) one comprising a solution of a poorly water-soluble drug or compound in a water-miscible solvent, or mixtures thereof at a suitable concentration of the said drug; and b) the other comprising a solution of the polymer of the present invention, of high purity and substantially free of monomeric contaminants, along with pharmaceutically acceptable excipients in an aqueous solvent, generally water of injection grade, both the vials being sterile and manufactured and packed under aseptic conditions.

The contents of the two vials are then added to the diluting fluid prior to administration to humans/animals.

Optionally, the kit can further comprise a diluting fluid, and a syringe and a needle having an internal diameter in the range of 0.305 to 0.356 mm, if a small volume, say 1-5 ml of the contents of vial a) are to be added to about 35 times its volume of the contents of vial b) or a syringe and a needle having an internal diameter in the range of 0.559 to 0.711 mm, if a larger volume, say 10-15 ml of the contents of vial a) are to be added to about 35 times its volume of the contents of vial b).

Especially in the case of a kit comprising Paclitaxel, for administration to patients for treatment of breast cancer, the two vial kit presentation would comprise of:

a) one vial containing a solution of 400 mg of Paclitaxel in 20 ml of ethanol;

b) the other containing a solution containing 200 mg of the polymer of the present invention, of high purity and substantially free of monomeric contaminants, along with pharmaceutically acceptable excipients in 20 ml of water, and optionally, the kit can further comprise a 500 ml bottle of 10% Dextrose solution, and a syringe and a needle having an internal diameter of 0.711 mm, for injection of the solution of vial a) to the 500 ml bottle of 10% Dextrose solution, to which has been added the solution of vial b) in a time period not exceeding 10 seconds, preferably in a time period of 6 to seconds to produce a pharmaceutical composition suitable for administration in nanoparticles of consistent particle sizes, with minimal or negligible size variation and consistent loading of the drug, within the polymeric shell, and longer stability.

TABLE V

Effect Of The Time Of Addition Of A Solution Of Poorly Water-Soluble Drugs Or Compounds And Internal Diameter Of The Needles Through Which Such Solutions Are Added To A Solution Of The Polymer And Other Excipients In A Diluting Fluid

| Sr. No. | Poorly Water-Soluble Drug Or Compound; The Solvent In Which It Is Dissolved; And The Volume Of Solution Injected | Internal Diameter (in mm) Of The Needle Through Which The Solution Of The Poorly Water-Soluble Drug Or Compound Is Added To The Solution Of The Polymer And Excipients In A Diluting Fluid | Addition Time (In Secs). Of The Solution Of Poorly Water-Soluble Drug Or Compound To The Solution Of The Polymer And Excipients In A Diluting Fluid (In ml) | Average Particle Size (nm) | Stability (Hrs) | Clarity Of The Solution |
|---|---|---|---|---|---|---|
| 1 | Paclitaxel/Ethanol (1 ml) | 0.305 | 3 Secs/≈35 ml | 80 | >24 | Clear |
| 2 | Paclitaxel/Ethanol (1 ml) | 0.467 | 2 Secs/≈35 ml | 90 | 20 | Very Slight Opalescence |
| 3 | Paclitaxel/Ethanol (1 ml) | 0.711 | 2 Secs/≈35 ml | 135 | <10 | Slight Opalescence |
| 4 | Paclitaxel/Ethanol (1 ml) | 1.270 | 2 Secs/≈35 ml | 270 | <4 | Opalescent |
| 5 | Paclitaxel/Ethanol (1 ml) | 0.305 | 6 Secs/≈35 ml | 240 | <4 | Slight Opalescence |
| 6 | Paclitaxel/Ethanol (1 ml) | 0.467 | 6 Secs/≈35 ml | 280 | <2 | Highly Opalescent |

TABLE V-continued

Effect Of The Time Of Addition Of A Solution Of Poorly Water-Soluble Drugs Or Compounds And
Internal Diameter Of The Needles Through Which Such Solutions Are Added To A Solution Of The
Polymer And Other Excipients In A Diluting Fluid

| Sr. No. | Poorly Water-Soluble Drug Or Compound; The Solvent In Which It Is Dissolved; And The Volume Of Solution Injected | Internal Diameter (in mm) Of The Needle Through Which The Solution Of The Poorly Water-Soluble Drug Or Compound Is Added To The Solution Of The Polymer And Excipients In A Diluting Fluid | Addition Time (In Secs). Of The Solution Of Poorly Water-Soluble Drug Or Compound To The Solution Of The Polymer And Excipients In A Diluting Fluid (In ml) | Observations/Results | | |
|---|---|---|---|---|---|---|
| | | | | Average Particle Size (nm) | Stability (Hrs) | Clarity Of The Solution |
| 7 | Paclitaxel/Ethanol (1 ml) | 0.711 | 6 Secs/≈35 ml | 285 | <2 | Highly Opalescent |
| 8 | Paclitaxel/Ethanol (1 ml) | 1.270 | 6 Secs/≈35 ml | 2300 | <0.5 | Milky |
| 9 | DRF-4012 of Formula (III)/Ethanol (1 ml) | 0.305 | 3 Secs/≈35 ml | 70 | >24 | Clear |
| 10 | DRF-4012 of Formula (III)/Ethanol (1 ml) | 0.465 | 2 Secs/≈35 ml | 90 | 20 | Very Slight Opalescence |
| 11 | DRF-4012 of Formula (III)/Ethanol (1 ml) | 0.711 | 2 Secs/≈35 ml | 100 | <10 | Slight Opalescence |
| 12 | DRF-4012 of Formula (III)/Ethanol (1 ml) | 1.270 | 2 Secs/≈35 ml | 130 | <6 | Opalescent |
| 13 | DRF-4012 of Formula (III)/Ethanol (1 ml) | 0.305 | 6 Secs/≈35 ml | 200 | <6 | Slight Opalescence |
| 14 | DRF-4012 of Formula (III)/Ethanol (1 ml) | 0.467 | 6 Secs/≈35 ml | 200 | <4 | Highly Opalescent |
| 15 | DRF-4012 of Formula (III)/Ethanol (1 ml) | 0.711 | 6 Secs/≈35 ml | 240 | <2 | Highly Opalescent |
| 16 | DRF-4012 of Formula (III)/Ethanol (1 ml) | 1.270 | 6 Secs/≈35 ml | 8100 | <0.5 | Milky |
| 17 | Paclitaxel/Ethanol (15 ml) | 0.711 | 10 Secs/≈500 ml | 85 | >24 | Clear |
| 18 | Paclitaxel/Ethanol (15 ml) | 0.711 | 15 Secs/≈500 ml | 150 | <15 | Slight Opalescence |
| 19 | Paclitaxel/Ethanol (15 ml) | 0.330 | 18 Secs/≈500 ml | 50 | 20 | Clear |

In summary, the present invention, as mentioned hereinbefore, is a step forward in providing a solution to most, if not all of the limitations of the prior art methods in the field of nanoparticle technology and provides:

i) A polymer comprising three monomeric units selected from NIPAM, VP, and MPEG, of high purity and substantially free of monomeric contaminants, with the level of toxic NIPAM and VP in the polymer <0.001%; which, moreover, has been established to be biocompatible, non-biodegradable, safe and non-toxic for human/animal use;

ii) A highly selective method for preparation of the polymer comprising three monomeric units selected from NIPAM, VP, and MPEG, of high purity and substantially free of monomeric contaminants, with the level of toxic NIPAM and VP in the polymer <0.001% comprising subjecting an aqueous solution of the polymer thus prepared to diafiltration;

iii) A pharmaceutical composition of poorly water-soluble drugs or compounds in nanoparticulate form, comprising the polymer of high purity and substantially free of monomeric contaminants along with pharmaceutically acceptable excipients, which is safe and non-toxic and hence highly suitable for human/animal use or administration;

iv) A highly selective method for production of a pharmaceutical composition of poorly water-soluble drugs or compounds in nanoparticulate form, comprising the polymer of high purity and substantially free of monomeric contaminants along with pharmaceutically acceptable excipients, having consistent particle sizes of the nanoparticles and consistent drug loading; and v) A pharmaceutical composition of poorly water-soluble drugs or compounds in nanoparticulate form, comprising the polymer of high purity and substantially free of monomeric contaminants along with pharmaceutically acceptable excipients, having consistent particle sizes of the nanoparticles with higher drug loading and a longer stability.

DETAILED DESCRIPTION OF THE INVENTION

A. Preparation of the Polymer of the Present Invention

The polymer of the present invention comprises of the three monomeric units selected from NIPAM, VP and MPEG, wherein the polymer chains are cross-linked with a cross linking agent, which does not contain any suithydryl groups or disulfide bonds.

The cross-linking agent plays an important role during polymerization by providing cross-links into the linear polymer chains and is in general a bi-functional vinyl derivative, whenever used. It can be more than bi-functional i.e. it can have more than two reactive sites. A bi-functional vinyl derivative that can be advantageously employed is N,N'-Methylene bis acrylamide (MBA), which is preferred.

The polymer of the present invention can be prepared by general methods normally adopted for polymerization reactions.

In a particular embodiment, the polymer of the present invention can be prepared by subjecting the monomers N-Isopropylacrylamide (NIPAM), 1-Vinyl-2-pyrrolidone (VP) and Polyethylene glycol (mol. wt 6000) ester of Maleic anhydride (MPEG) for free radical polymerization in presence of an activator, a polymerization initiator, and a cross-linking agent in aqueous medium.

A combination of monomers, N-isopropyl acrylamide (NIPAM) and Vinylpyrrolidone (VP) could be employed in the weight ratio ranging between 55:22 to 65:35, while the comonomeric composition of (NIPAM+VP):MPEG that can be employed is in the range of 80:20 to 95:5. More particularly and preferably, a combination of monomers—N-isopropyl acrylamide (NIPAM) and Vinylpyrrolidone (VP) is employed in the weight ratio ranging between 58:32 to 62:28 and the comonomeric composition of (NIPAM+VP):MPEG is employed in the range of 90:10 or 95:5, which is found to impart the desired biocompatibility, non-biodegradability and biologically safe profile to the polymers, for the reason that this particular ratio consistently results in formation of a randomly hyperbranched co-polymeric unit of NIPAM and VP, which are stabilized by an outer shell coating formed from hydrogen-bonding by the diester adduct (major) and monoester adduct (minor) of maleic anhydride-polyethylene Glycol (MPEG).

The polymerization initiators play an important role in initiation of free radical formation. The initiators that can be employed can be peroxide compounds, such as diacyl peroxide, benzoyl peroxide, diacetyl peroxide, dialkyl peroxides, tertiary butyl peroxide and tertiary amyl Peroxide or nitrile based polymerization initiators such as 2,2'-Azobis isobutyronitrile (AIBN) or inorganic salt based polymerization initiators such as Ammonium perdisulphate or Ammonium persulphate (APS), used either alone or in combination.

Amongst the abovementioned polymerization initiators, Ammonium persulphate (APS) is the preferred one.

Although, polymerization initiators initiate the polymerization, however, the polymerization reaction is found to be accelerated by the presence of activating agents (often known as Activators) which catalyze the formation of free radicals from polymerization initiators. Such activators may be selected from Tetramethylethylene diamine (TMED) and Ferrous Ammonium Sulphate (FAS), of which a combination of TMED and FAS is preferred. Any combination of the polymerization initiator and the activator can be employed for the polymerization reaction. Two or more initiators can also be used. Similarly, two or more activators can also be employed.

As mentioned hereinbefore, the cross-linking agent plays an important role during polymerization by providing cross-links into the linear polymer chains and is in general a bi-functional vinyl derivative, whenever used. It can be more than bi-functional i.e. it can have more than two reactive sites. A bi-functional vinyl derivative that can be used is N,N'-methylene bis acrylamide (MBA), which is preferred.

The polymerization is carried out in the presence of an inert gas, which can be nitrogen or argon.

Generally, the polymerization reaction is carried out, first by dissolving an appropriate quantities of the respective monomers viz, N-Isopropylacrylamide (NIPAM), 1-Vinyl-2-pyrrolidone (VP) and Polyethylene glycol (mol. wt 6000) ester of Maleic anhydride (MPEG) in an aqueous solvent, which in general is water. To the aqueous solution of the respective monomers thus obtained is added in succession an aqueous solution of a cross-linking agent and an activator. The solution is de-aerated by bubbling an inert gas for about 30-60 minutes. To the de-aerated solution is added an aqueous solution of polymerization initiators and the solution is subjected to polymerization at a temperature of between 25° to 45° C., preferably at a temperature between 25° to 35° C. under continuous inert gas bubbling for a period of time till the polymerization is complete.

The cross-linking agent can be employed in quantities in the range of between 1.3-1.5% w/w of the total monomer content, and more preferably in the range of between 1.35-1.4% w/w of the total monomer content.

Activators can be employed in quantities in the range between 15-18% w/w of the total monomer content and more preferably in the range between 15-16% w/w of the total monomer content.

The polymerization initiator can be employed in quantities in the range of between 20-30% w/w of the total monomer content and more preferably in the range of between 23-25% w/w of the total monomer content.

The progress of the polymerization reaction is monitored by HPLC and usually gets completed in about 3-6 hours.

After completion of the polymerization reaction, the solution is subjected to filtration through pre-sterilized, disposable 0.2 µm Polyethersulphone membrane 1" capsule filters, 0.8 and 0.2 µm pore size; Type DPS-5101AA-201 (Make: M/s Advanced Microdevices Pvt. Ltd, India). The filtered contents of the reaction vessel are subjected to Diafiltration using Proflux M12 (Millipore) diafiltration device to remove monomeric contaminants and other low molecular weight impurities.

The diafiltration is generally completed in less than one hour and normally results in not only a solution substantially free of monomeric contaminants but also in a concentrated form, usually one-forth to one-sixth ($\frac{1}{4}^{th}$ to $\frac{1}{6}^{th}$) of the initial volume of the solution subjected to diafiltration. If necessary, the concentrated solution, thus obtained, which is substantially free of monomeric contaminants, can be subjected to another cycle of diafiltration. The concentrated solution of polymer of the present invention of high purity and substantially free of monomeric contaminants can be subjected to a step of lyophilization to obtain the polymer in solid lyophilized form for utilization in pharmaceutical compositions or the concentrated solution as such can be directly utilized for formulation of the said pharmaceutical compositions.

In a typical embodiment, the polymerization reaction is carried out, by dissolving an appropriate quantity of the respective monomers viz, N-Isopropylacrylamide (NIPAM), 1-Vinyl-2-pyrrolidone (VP) and Polyethylene glycol (mol. wt 6000) ester of Maleic anhydride (MPEG) in water. To the aqueous solution of the respective monomers thus obtained, is added an appropriate volume of aqueous solution (about 5% w/v) of a cross-linking agent, N,N'-methylene bis acrylamide (about 1.37% w/w of the total monomer content) and a combination of activators, comprising an appropriate volume of Tetramethylethylene diamine (TMED, about 15.4% w/w of the total monomer content) and an aqueous solution (0.5% w/v) of Ferrous Ammonium Sulphate (about 0.1% w/w of the total monomer content). It is preferable to add one of the activators first and the other one along with the polymerization initiator, which is added later. The solution is de-aerated by bubbling nitrogen for about 30 minutes. To the de-aerated solution is added an appropriate volume of an aqueous solution (about 80% w/v) of polymerization initiators, Ammonium persulphate (about 24% w/w of the total monomer content) and the solution is subjected to polymerization at a temperature preferably between 25° to 35° C. under continuous nitrogen bubbling for a period of time till the polymerization is complete. Usually, the polymerization reaction gets completed in 3-5 hours.

After completion of the polymerization reaction, the solution is subjected to filtration through pre-sterilized, disposable 0.2 µm Polyethersulphone membrane 1" capsule filter (0.8+0.2 μm pore size). The filtered contents of the reaction vessel are subjected to diafiltration to remove monomeric contaminants and other low molecular weight impurities.

In a typical embodiment, a solution of the polymer in water at a concentration of say 1 gm in 50 ml could be subjected to diafiltration, whereupon, after the diafiltration a concentrated solution of the polymer in about one-fourth to one-sixth ($1/4^{th}$ to $1/6^{th}$) of the initial volume, say 1 gm of the polymer in about 12-13 ml of water is obtained, which contains less than 0.001% w/w of both NIPAM and VP.

The detection and quantification of the residual monomers, especially residual VP and NIPAM in the polymer were carried out by HPLC. The HPLC system that can be used for detection of the monomers is Agilent 1100 series or equivalents, using Reverse Phase RP-18 (C-18) columns [Lichrospher RP-18e, 5μ, 250 mm×4 mm]. The Mobile Phase used is a mixture of water and acetonitrile in a ratio of 80:20, at a flow rate of 1 ml/min, with a sample injection volume is 50 μl.

The run time is 10 mins and the column temperature is 30° C. and the Detector wavelength is 226 nm.

Under the above conditions, NIPAM had a retention time of about 3 minutes, whereas VP had a retention time of about 5 minutes.

The concentrated solution of polymer so obtained is of high purity and substantially free of monomeric contaminants, which can be subjected to a step of lyophilization to obtain the polymer in solid lyophilized form for utilization in pharmaceutical compositions or the concentrated solution as such can be directly utilized for formulation of the said pharmaceutical composition. It is however preferable to utilize the concentrated solution of the polymer as such for formulation into pharmaceutical compositions.

B. Characterization of the Polymer of the Present Invention

The polymer of the present invention obtained by the method mentioned hereinbefore was subjected to extensive spectroscopic analysis such $^1$H-NMR, $^{13}$C-NMR, Fourier Transform Infrared (FT-IR) and Thermal analysis such as Differential Scanning calorimetry (DSC) and Thermo Gravimetric analysis (TGA) etc. to elucidate the structure of the polymer thus obtained.

The $^1$H NMR spectrum of the polymer of the present invention in $CDCl_3$ shows peaks at the δ (ppm) of 1.14 (br, —CH$(CH_3)_2$); 1.45 (br, —$CH_2$—CH—N (VP-Ring); 1.63 (br, —$CH_2$—CHC(=O)NH); 1.99 (br, —CH C(=O)NH—), $CH_2$ (VP ring), 2.36 ($CH_2$, VP ring), 3.0 (—O—$CH_2$—$CH_2$—), 3.23 ($CH_2$—N—); 3.62-3.66 (Br, $CH_2$, MPEG); 3.72 (NH—CH$(CH_3)_2$); 3.97 (Br, CH). The $^1$H-NMR spectrum of the polymer of the present invention is summarized in FIG. 1.

Figure 2:
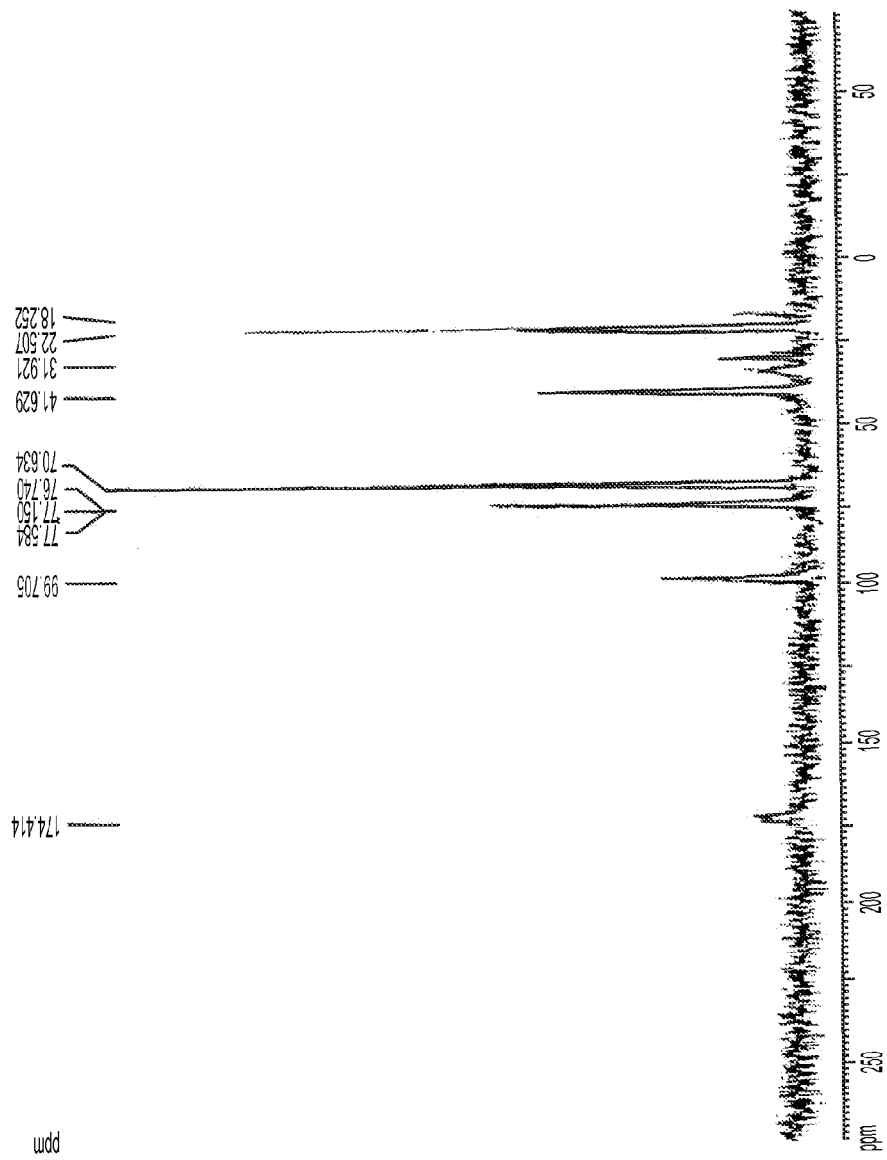
FIG. 2: The $^{13}$C-NMR Spectrum of the Polymer of the present invention.

The $^{13}$C NMR spectrum of the polymer of the present invention shows peaks at the δ (ppm) of 174 (C=O); 76.6-77.6 (multiplet for $CDCl_3$ and CFI for polymer backbone); 70.6 ($CH_2$'s MPEG); 41.6 (CH for isopropyl unit); 31.8 ($CH_2$'s, polymer backbone); 22.6 ($CH_3$'s, isopropyl). The $^{13}$C-NMR spectrum of the polymer of the present invention is summarized in FIG. 2.

Figure 3:
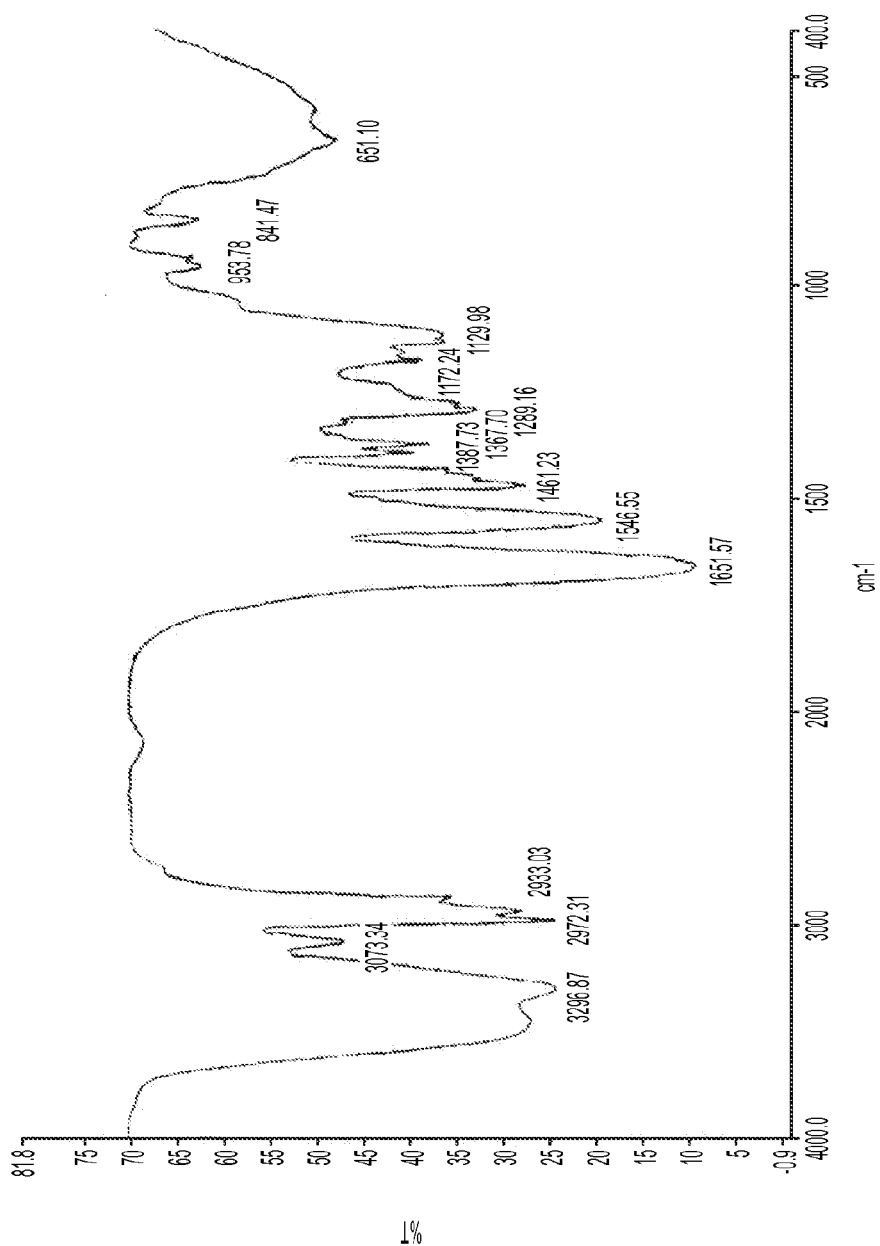
FIG. 3: The Fourier Transform Infrared (FT-IR) Spectrum of the Polymer of the present invention.

The Fourier Transform Infrared (FT-IR) spectrum of the polymer of the present invention shows peaks at the following frequency values (cm$^{-1}$) of 3500 (s, OH); 3296 (s, NH, sec-Amide); 2972-2933 (s, CH, $CH_2$, $CH_3$); 1651 (br, strong, split peaks ester C=O and C=O of amide I); 1546 (s, NH bend of Amide II and possibly C=O of free acid, minor); 1387, 1367 (doublet of Isopropyl groups, $CH_3$, deformation), 1172-1129 (m, O—C—O). The Fourier Transform Infrared (FT-IR) spectrum of the polymer of the present invention is summarized in FIG. 3.

These characterization studies confirm that the polymer of the present invention has the structure, which is depicted in hereinbelow as formula (I):

Further, in order to characterize the physicochemical properties of the polymer in detail, various properties of the polymer such as thermal properties, Critical Micelle Concentration (CMC), solubility and pH, storage stability were evaluated.

Figure 4:
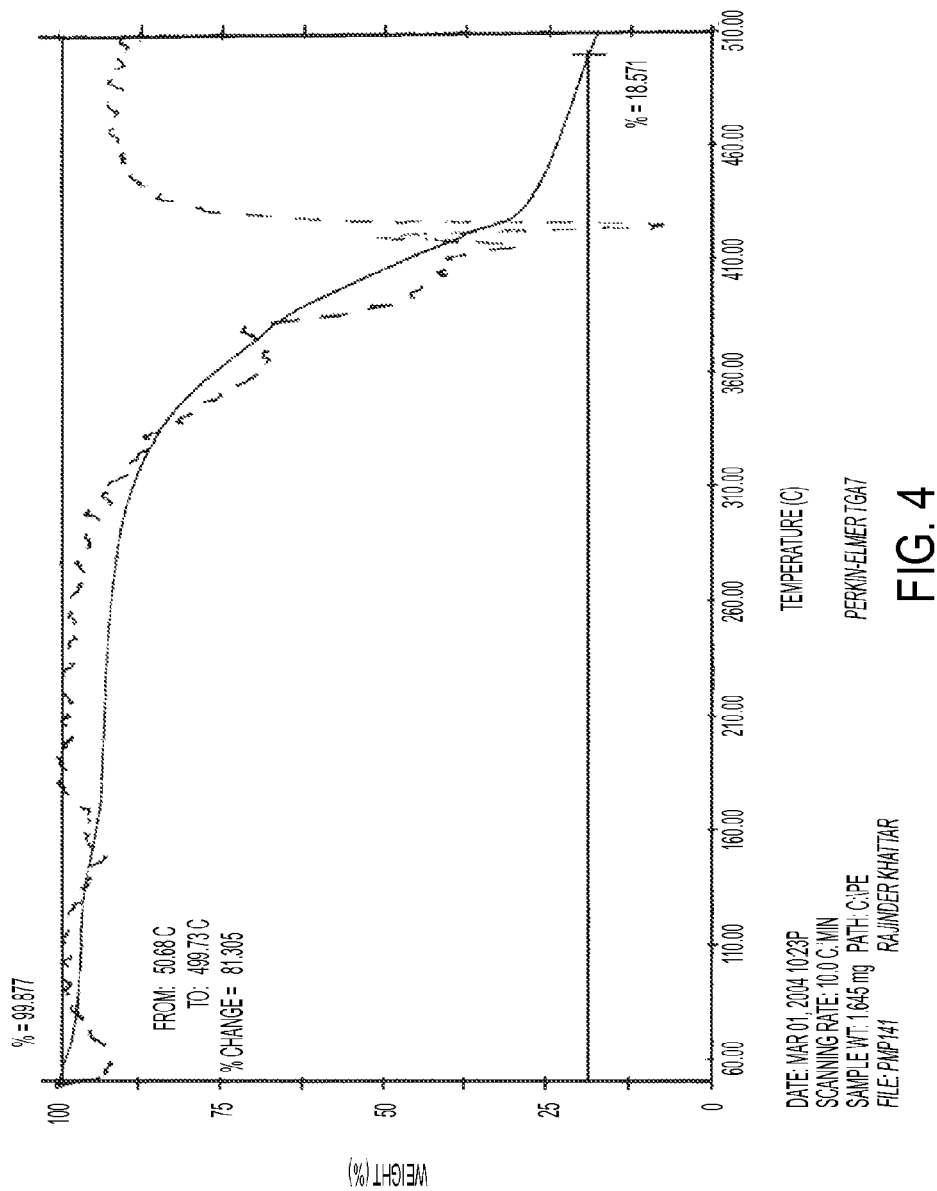
FIG. 4: The TGA Thermogram of the Polymer of the present invention.

Thermogravimetric analysis (TGA), showed that there is some weight loss from 51-260° C., which indicates loss of solvent and some macromolecular reactions that might be occurring especially in the MPEG units of the polymer before degradation starts occurring at around 310° C. This indicates that the polymer has high thermal stability, which in great part may be provided by the MPEG units. The TGA thermogram of the polymer of the present invention is summarized in FIG. 4.

Figure 5:
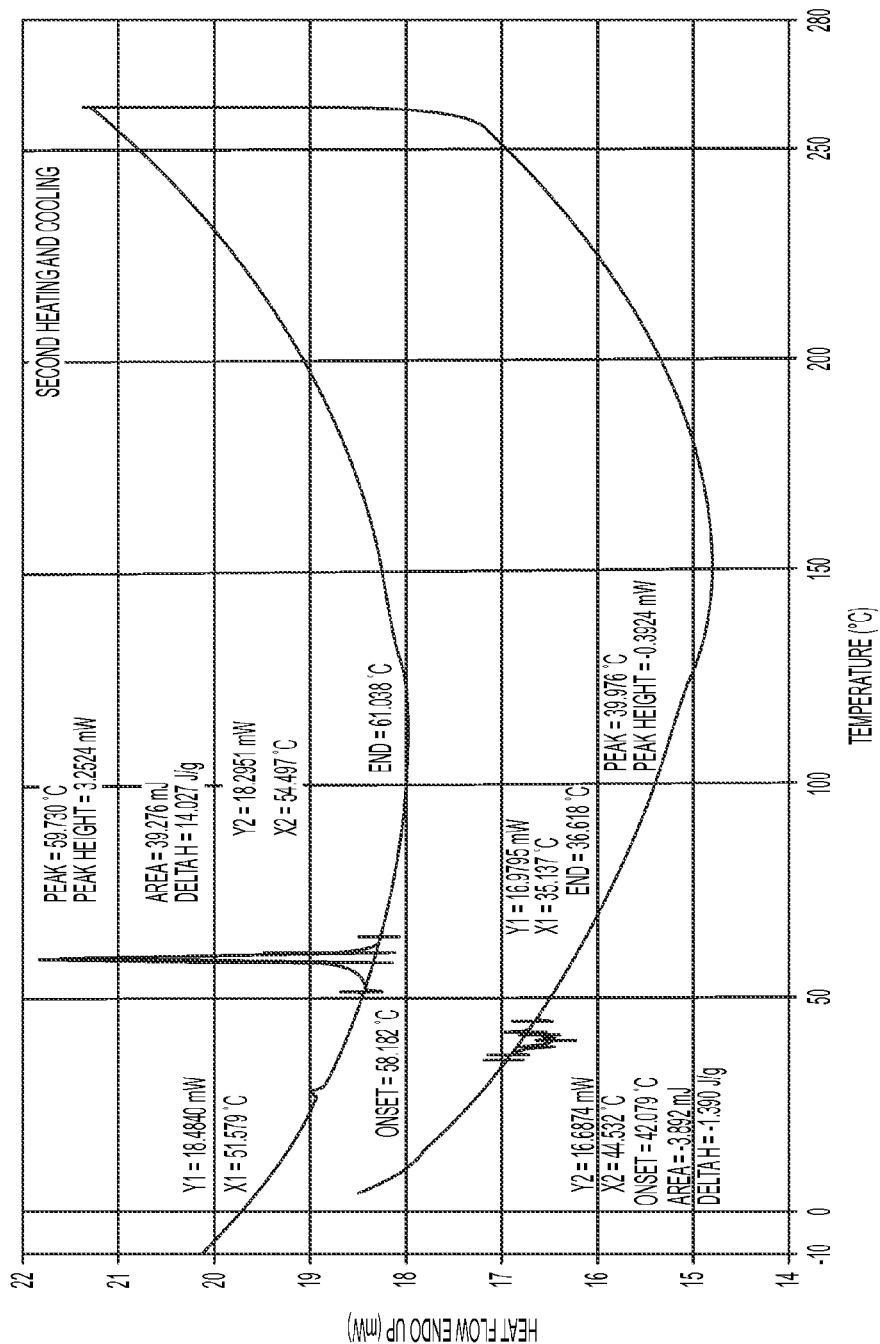
FIG. 5: The DSC Thermogram of the Polymer of the present invention.

Further, the Differential Scanning calorimetry (DSC) profile of the polymer, represented in FIG. 5 did not show any glass transition temperature (Tg), but only a melting temperature (Tm) of 58° C. and a recrystallization point temperature ($T_C$) of 38.4° C. were observed. The absence of any clear Tg may be indicative of a highly rigid hyperbranched structure, which could also be contributed by extensive hydrogen bonding with MPEG.

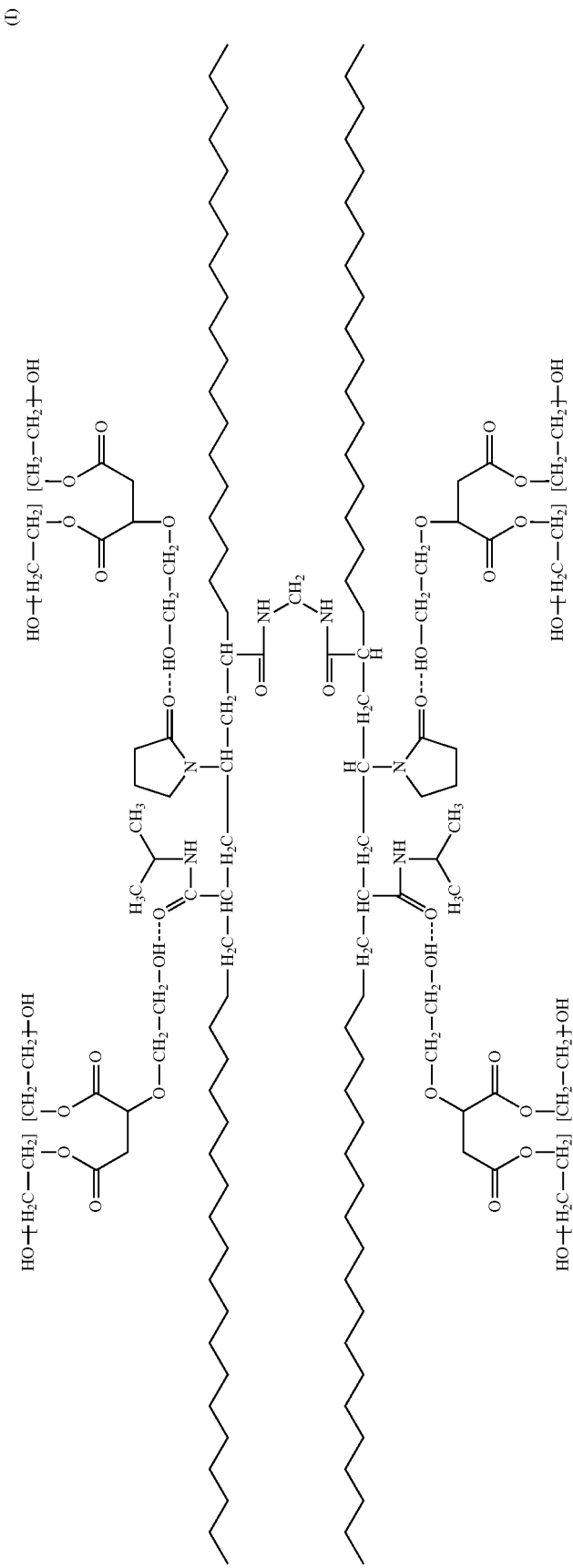

Structure of the Polymer of the Present Invention

Lower Critical Solution Temperature (LCST) of the polymer has values in the region of 50-60° C. Again this is an important parameter for amphiphilic polymers in aqueous phase manifesting in thermo-responsive phase transitions at a certain temperature called LCST. Below the LCST the polymer would exhibit a soluble extended chain configuration i.e. hydrophilic behaviour. Above the LCST, the polymer undergoes a phase transition to conform to forming an insoluble, hydrophobic aggregate. This property is useful to determine the ability to form micelles in the appropriate solvent and act in delivery systems for the drugs in pharmaceutical applications.

Critical Micelle Concentration (CMC) is another important parameter that defines the encapsulating ability of a nano-carrier and determines the stability. This is the lowest concentration for the amphiphilic polymer or unimers to form a micellar structure capable of encapsulating a drug in its hydrophobic core. The CMC value for present polymer is about 0.2 mg/ml. Further, the polymer comprising of thermosensitive and pH sensitive monomers such as N-isopropylacrylamide (NIPAM) and 1-Vinyl Pyrrolidin-2-one (VP) are well known as biocompatible with proteins and blood cells. Further, biomedical applications of poly (NIPAM) are quite widespread due to its reversible temperature transition i.e. LCST, excellent Hydrogen-bonding, micellar and hydrogel forming capabilities. Similarly, Poly Vinylpyrrolidone (also known as Povidone) polymers are also highly water soluble and form extensive Hydrogen—bonding with water. The intended application of this polymer was to design a novel incorporating system incorporating the strengths of the various pre-defined monomers leading to the formation of a thermo-sensitive, pH sensitive, stable polymeric nanoparticles containing hydrophilic and hydrophobic groups to solubilize the drugs that are poorly soluble in water.

Very surprisingly, it was found that, the formation of a randomly hyperbranched co-polymeric unit consisting of NIPAM and VP stabilized by an outer shell coating formed from hydrogen-bonding by diester adduct (major) and monoester adduct (minor) of maleic anhydride-polyethylene Glycol (MPEG) having the comonomeric composition of (NIPAM+VP):MPEG in the range of 80:20 to 95:5 as well as NIPAM:VP units in the range of 55:22 to 65:35 imparts the desired biocompatibility, non-biodegradability and biologically safe profile to polymers. Specifically, it was found that better results (higher LCST, higher yield, percentage release from Paclitaxel nanoparticles) were obtained when the composition of (NIPAM+VP):MPEG is in the range of 90:10 or 95:5 and NIPAM: VP units are used in the range of 58:32 to 62:28. The ratio of the monomer used is also consistent in the final polymer and is confirmed by various studies such as $^1$H-NMR, $^{13}$C-NMR and Fourier Transform Infrared (FT-IR) spectral studies C. Biocompatibility and Non-Biodegradability of the Polymer of the Present Invention When Pharmacokinetics, Biodistribution and Elimination of [$^{14}$C]-labelled polymer was evaluated using male swiss albino mice, the radioactive blood concentration profile revealed phasic curve (FIG. 6), with short elimination half-life $T_{1/2}(\beta)$ of 0.448±0.157 hours (26.88 min) and rapid clearance of 54.7 ml/hr. The results of this study are summarized in Tables—VI and VII.

TABLE VI

Pharmacokinetic Parameters Of The Polymer Of The Present Invention

| Parameter | Estimate ± SE |
|---|---|
| $T_{1/2}$(K10) | 0.152 ± 0.018 hr |
| $T_{1/2}$(alpha) | 0.065 ± 0.014 hr |
| $T_{1/2}$(beta) | 0.448 ± 0.157 hr |
| $C_{max}$ | 82.96 ± 5.11 µg/mL |
| AUC | 18.29 ± 1.62 hr × µg/ml |
| CL | 54.67 ± 4.86 ml/hr |
| MRT | 0.465 ± 0.13 hr |
| $V_{ss}$ | 25.43 ± 5.2 ml |

The dominant route of elimination was found to be urine (urine, 66.91% vs feaces, 17.39% at 48 hrs) and recovery data collected up to 48 hrs accounts for 84.87% of radioactivity injected. Tissue distribution was negligible. The kidney, liver, skin and intestine were found to be the target organs. However, the level of the polymer in tissues was rapidly cleared via urine and faeces.

TABLE VII

Recovery of Radio-labelled Polymer Of The Present Invention

| | Percentage (%) of dose | | | |
|---|---|---|---|---|
| Time | 0-10 min | 0-1 hr | 0-24 hrs | 0-48 hrs |
| Urine | 27.14 | 61.64 | 64.56 | 66.91 |
| Feaces | 0.10 | 0.65 | 12.29 | 17.39 |
| Tissues | 15.50 | 3.22 | 0.78 | 0.57 |
| Rinse | 5.04 | 2.27 | 0.84 | 0.00 |
| Total | 47.16 | 67.78 | 78.47 | 84.87 |

Thus, in conclusion, the polymer is found to be rapidly eliminated from the body without being deposited and degraded in vital organs suggesting the safety and utility of the polymer for human use.

D. Toxicity Studies on the Polymer of the Present Invention

Toxicity studies of Polymer of formula (I) were carried out to evaluate:

(i) Localised Toxicity (Subcutaneous and Intravenous);

(ii) Target Organs Dose Toxicity up to 800 mg/kg animal body weight; and (iii) Six Months Cyclical dose toxicity D(i) Localised Toxicity (Subcutaneous and Intravenous)

The toxicity of the polymer was determined after a single subcutaneous administration of 100 µl of 75-mg/ml of the polymer in the rabbit ear, which caused mild inflammation at the site of injection, when tested after 48 hrs post injection, suggesting that the present polymer does not cause any local toxicity at the site of administration following subcutaneous administration.

The toxicity of the present polymer was determined for a five day continuous intravenous administration of 75-mg/ml of present polymer at a dose of 125 mg/kg in rabbit ear vein and similar results were obtained, further confirming that the present polymer does not cause any local toxicity at the site of administration.

Figure 7:
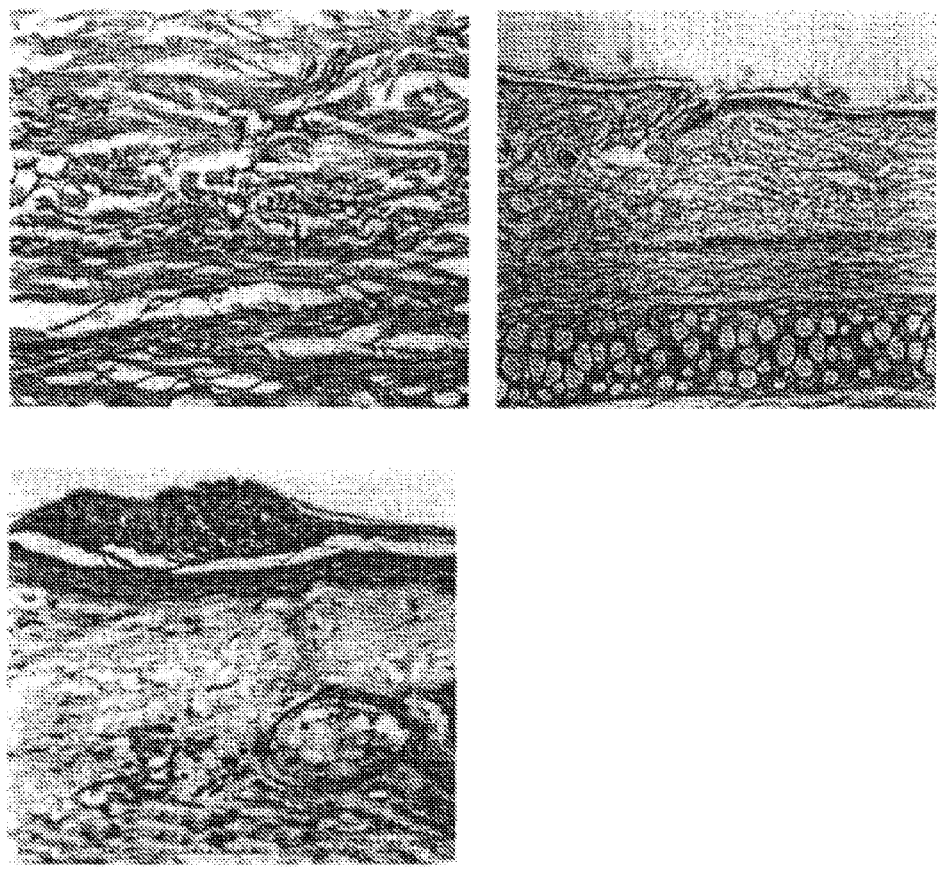
FIG. 7: Photographs of S&E stained Rabbit Ear Lobe site after 48 hours of the subcutaneous administration of a 10% Dextrose solution (Control).
Figure 8:
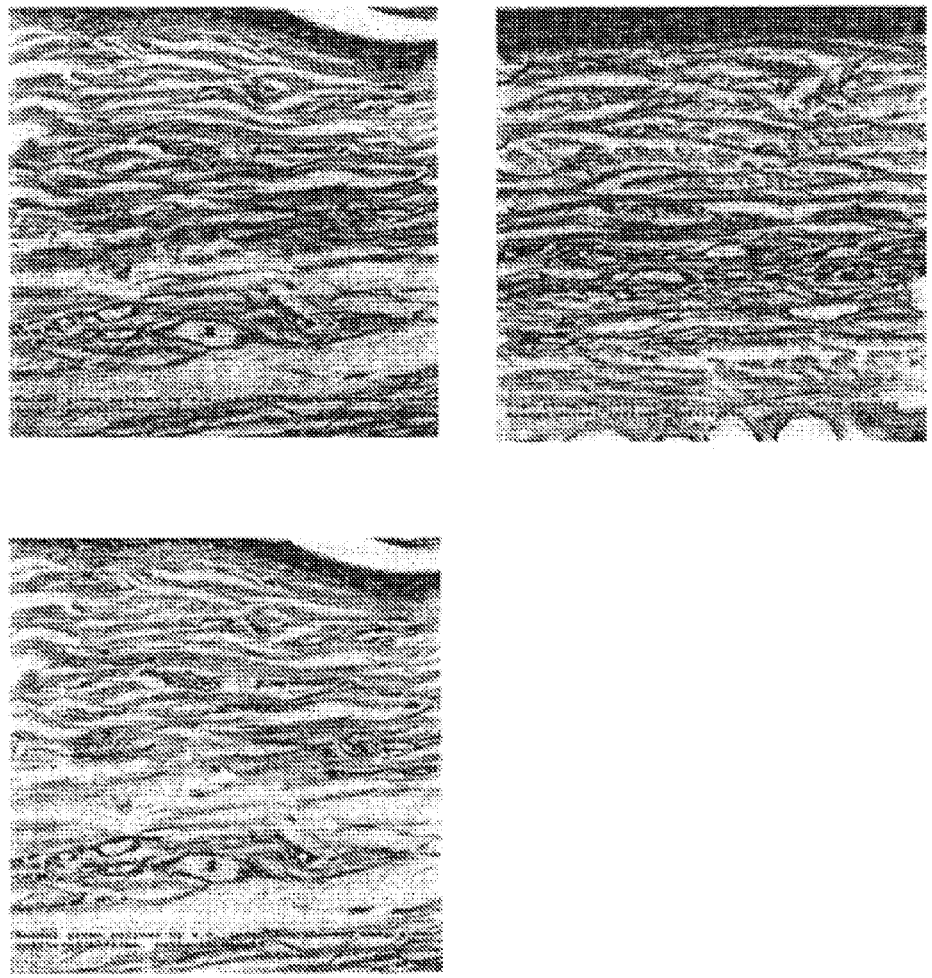
FIG. 8: Photographs of S&E stained Rabbit Ear Lobe site after 48 hours of the subcutaneous administration of an aqueous solution of the Polymer of the present invention.

Representative photographs of S&E stained Rabbit Ear Lobe site after 48 hours of subcutaneous injection with 10% Dextrose solution is shown in FIG. 7 and photographs of S&E stained Rabbit Ear Lobe site after 48 hours of subcutaneous injection with an aqueous solution of the polymer is shown in FIG. 8.

Figure 9:
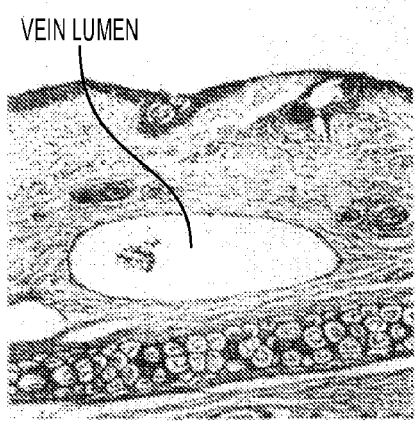
FIG. 9: Photographs of S&E stained Rabbit's Marginal Ear Vein site after 24 hours of the Intravenous administration of a 10% Dextrose solution (Control).
Figure 9:
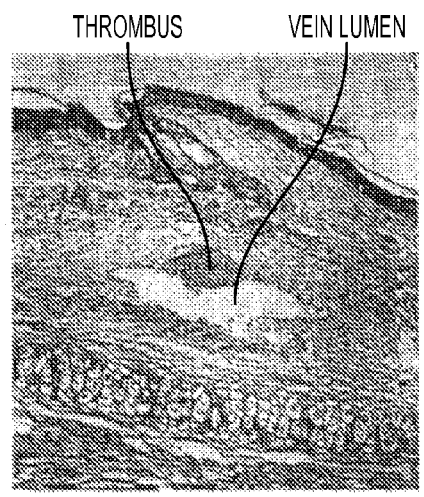
Figure 9:
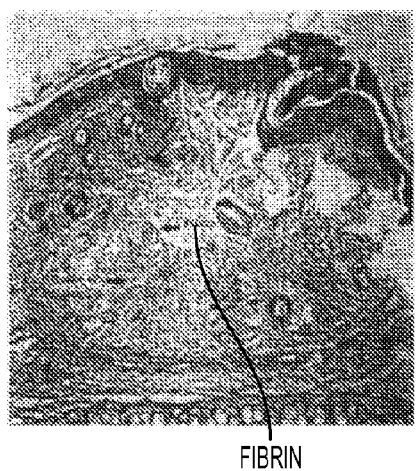
Figure 9:
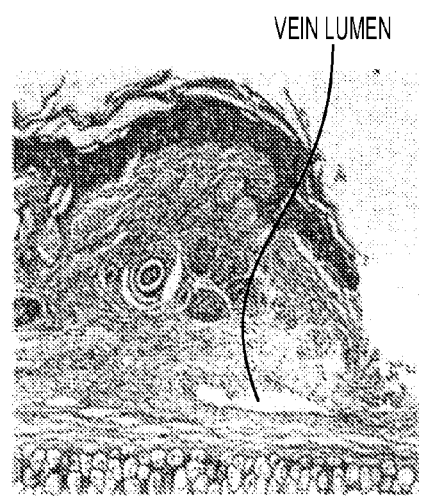
Figure 10:
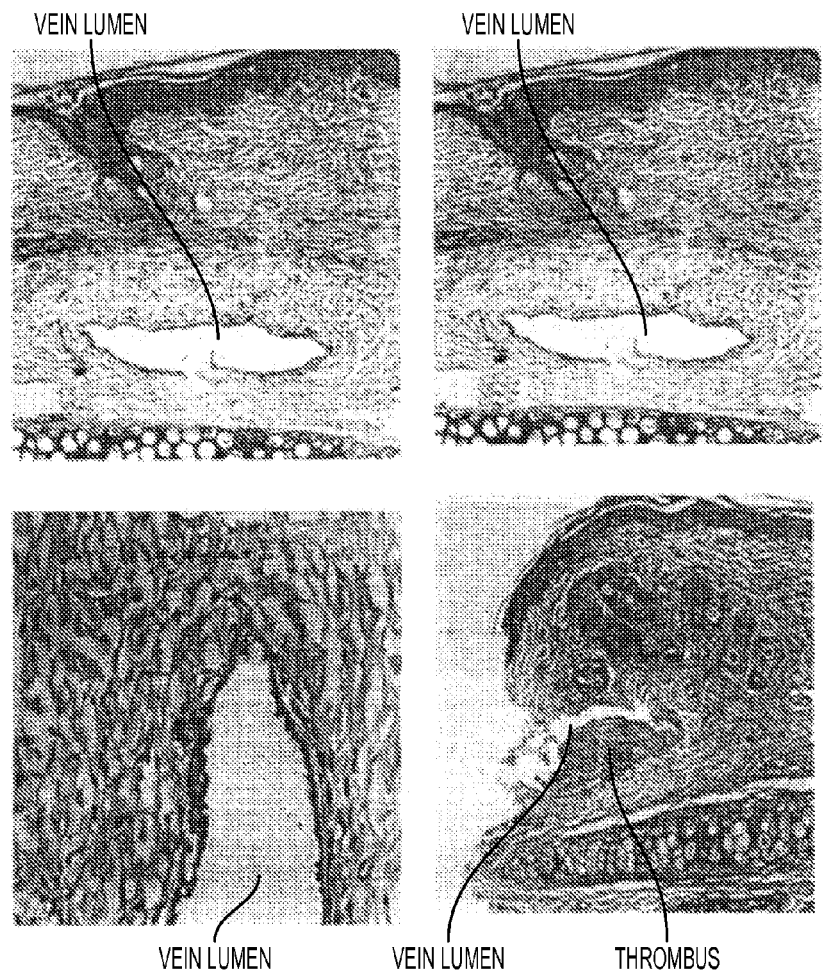
FIG. 10: Photographs of S&E stained Rabbit's Marginal Ear Vein site after 24 hours of the Intravenous administration of an aqueous solution of the Polymer of the present invention.

Representative photographs of S&E stained Rabbit's Marginal Ear Vein site after 24 hours of intravenous injection with 10% Dextrose solution is shown in FIG. 9 and photographs of S&E stained Rabbit's Marginal Ear Vein site after 24 hours of intravenous injection with an aqueous solution of the polymer is shown in FIG. 10.

D(ii) Target Organs Dose Toxicity (Up to 800 mg/kg Animal Body Weight)

Further, the toxicity was evaluated on possible target organ(s) with special reference to microvasculature and determined by single intravenous bolus administration in Wistar Rats. The polymer was administered at two different dosages, viz. 400 mg/kg and 800 mg/kg. Under the conditions of study, single intravenous bolus administration of the present polymer at any dose does not produce any mortality or any observable toxic sign or symptoms in rats. Individual and Mean body weights of rats showed a steady increase in both Polymer treated and control groups. No significant difference was noted for body weight for treated animals at both doses as compared to that of the control.

In rats treated with the polymer, haematological parameters were within normal limits throughout the study. Biochemical parameters were also within the normal limits for the animals treated with both doses. The photoactometer test showed that there was no significant difference between the locomotor activity between the Control and Treated groups on day 7 and 21 respectively suggesting that the polymer does not have any neurotoxicity.

The Treated and Control group specimens showed similar histological features. Histology study was performed on vital organs such as liver, heart, lungs, kidneys, spleen, stomach, colon, thigh muscle and eye. All organs studied showed normal structure on light microscopic examination. The microvasculature in each organ was carefully examined and no pathological features were seen in any of the organs. Further, there were no changes in microvasculature of the polymer treated animals.

From the above observations, it was abundantly evident that polymer of the present invention at a dose of either 400 mg/kg or 800 mg/kg of body weight administered for five consecutive days did not cause any general toxicity or any significant haematological toxicity indicating the biologically safe and non-toxic profile of the present polymer.

D(iii) Six Months Cyclical Dose Toxicity

Further, six months cyclical dose toxicity was studied in rats by intravenous injection of polymer used in nanoparticle formulation. Male/Female Wistar rats were used for the study and dosing was done intravenously in the lateral tail vein cyclically once every three weeks for a period of 180 days (approximately 26 weeks). Animals of treated and control groups remained generally active and healthy during the period of study. The polymer concentration equivalent to 10 mg/kg of drug was found to be safe in the animals under study. Minimum alterations in haematology parameters noticed were within the normal range for Wistar rats and were not found to be treatment related.

The above studies suggest that the synthesised polymer is non-toxic and biologically safe for use in making pharmaceutical compositions.

E. Pharmaceutical Compositions Comprising the Polymer of the Present Invention

As discussed hereinbefore, the polymer of the present invention of formula (I), of high purity and substantially free of monomeric contaminants, in particular having residual monomeric NIPAM and VP<0.001% could be utilized to advantage for preparation of pharmaceutical compositions of poorly water-soluble drugs or compounds in nanoparticulate form, which are safe and non-toxic for human/animal administration or use.

In particular, the polymer of the present invention could be used to prepare a pharmaceutical composition in nanoparticulate forms, along with pharmaceutically acceptable excipients entrapping a host of poorly water-soluble drugs or compounds completely or near-completely within its polymeric shell.

Further, as discussed hereinbefore, poorly water-soluble drugs or compounds that can be utilized in the pharmaceutical compositions of the present invention are those generally having water solubility of less than 10 mg/ml.

Examples of such poorly water-soluble drugs or compounds include, but are not limited to, anticancer agents, anti-inflammatory agents, anti-fungal agents, antiemetics, antihypertensive agents, sex hormones, steroids, antibiotics, immunomodulators, anaesthetics etc. Typical examples of anticancer agents that can be entrapped within the polymeric shell are Paclitaxel, Docetaxel, and other related taxane derivatives; Irinotecan, Topotecan, and other related Camptothecin derivatives; Doxorubicin, Daunomycin, and related Anthracycline derivatives; Cisplatin; Oxaliplatin; 5-Fluorouracil; Mitomycin; Methotrexate; Etoposide; Betulinic acid and its derivatives; and Wedelolactone and its derivatives. Typical examples of anti-inflammatory agents that can be entrapped within the polymeric shell include Indomethacin, Ibuprofen, Ketoprofen, Flubiprofen, Piroxicam, Tenoxicam, and Naproxen. Typical examples of anti-fungal agents that can be entrapped within the polymeric shell include Ketoconazole, and Amphotericin B. Typical examples of sex hormones that can be entrapped within the polymeric shell include Testosterone, Estrogen, Progesterone, and Estradiol. Typical examples of steroids that can be entrapped within the polymeric shell include Dexamethasone, Prednisolone, and Triamcinolone. Typical examples of antihypertensive agents that can be entrapped within the polymeric shell include Captopril, Ramipril, Terazosin, Minoxidil, and Parazosin. Typical examples of antiemetics that can be entrapped within the polymeric shell include Ondansetron and Granisetron. Typical examples of antibiotics that can be entrapped within the polymeric shell include Metronidazole, and Fusidic acid. Typical examples of immunomodulators that can be entrapped within the polymeric shell include Cyclosporine; and Biphenyl dimethyl dicarboxylic acid. Typical examples of anaesthetics that can be entrapped within the polymeric shell include Propopol, Alfaxalone, and Hexobarbital A pharmaceutical composition of poorly water-soluble drugs or compounds typically comprises of a two kit-vial presentation, comprising in one hand, a vial containing a solution of a poorly water-soluble drug in a water-miscible solvent, or mixtures thereof, at a suitable concentration of the said drug or compound; and comprising on the other hand, a vial containing a solution of the polymer of the present invention, of high purity and substantially free of monomeric contaminants and pharmaceutically acceptable excipients in an aqueous solvent, generally water of injection grade, both the kit vials being sterile and manufactured and packed under aseptic conditions. The contents of the two vials are then added in succession to a diluting fluid for administration to humans/animals. It should be noted, as discussed hereinbefore as well as would be discussed hereinlater, the poorly water-soluble drug or compound gets entrapped within the polymeric shell of the polymer utilized therein and is produced in a nanoparticulate form of consistent size. The ratio of the solution of a poorly water-soluble drug in a water-miscible solvent, or mixtures thereof to the a solution of a poorly water-soluble drug in a water-miscible solvent, or mixtures thereof, contained in the two is generally between 1:1 to 1:10 by volume, preferably in a ratio of 1:1.

Optionally, the two kit-vial presentation can further comprise a diluting fluid, and a syringe and a needle of internal diameter in the range of between 0.305 to 0.356 or 0.559 to 0.711 mm, which depends on the volume of the drug solution and the volume of the diluting fluid containing the polymer and excipients to be mixed for administration to humans/animals in need thereof.

Suitable water-miscible solvents that can be utilized for dissolving the poorly water-soluble drug or compound include an aliphatic alcohol, specially ethanol; dialkyl amides, specially dimethyl formamide and dimethyl acetamide; dialkyl sufoxides, specially diemthyl sulfoxide and diethyl sulfoxide; polyethylene glycols of various molecular weights; polypropylene glycols of various molecular weights; surfactants, specially polysorbate 80, polysorbate 20, polyoxyethylated vegetable oil, and polyethoxylated castor oil; glycerine etc.

The pharmaceutically acceptable excipients that can be used to advantage include sodium deoxycholate; various bile salts; polysorbates of various grades, specially polysorbate 80, polysorbate 20, polyoxyethylated vegetable oil, and polyethoxylated castor oil; polysaccharides like dextrose, sucrose, lactose, mannitol etc.; sorbitan esters or spans of various grades; myrj of various grades; poloxomers of various grades etc., and a buffering agent for adjustment of the pH. Any buffering agent known in the art can be employed for adjustment of the pH of the solution, and in a preferred embodiment it is advantageous to utilize sodium citrate as the buffering agent.

Of the pharmaceutically acceptable excipients, sodium deoxycholate is preferred since it has an effect in stabilization of the pharmaceutical composition, whereas the buffering agent is used to adjust the pH of the perfusion fluid in the range of between 6.0 to 8.5, which is also found to have an effect in stabilization of the pharmaceutical composition.

The pharmaceutical composition can have a suitable loading or dose of the poorly water-soluble drug or compound and selection of an optimum loading or dose of the said drug or compound, largely depends on the nature of the drug or compound, its solubility as well as to the therapeutic disorder for which it is administered for. In the case of the pharmaceutically acceptable excipients, the proportion or quantity of that can be utilized in the pharmaceutical composition similarly, in turn depends on nature and loading of the poorly water-soluble drug or compound contained in the composition.

The pharmaceutical composition in nanoparticulate of poorly water-soluble drugs or compounds of the present invention can be prepared the following way:

i) Preparation of the drug concentrate, comprising dissolving the poorly water-soluble drug or compound in a suitable water-miscible solvent, or mixtures thereof;

ii) Preparation of an aqueous concentrate of the polymer and pharmaceutically acceptable excipients, comprising the steps of:
  a) first addition of the requisite amount of the polymer of formula (I), of high purity and substantially free of monomeric contaminants, specially having a level of toxic NIPAM and VP<0.001% to an appropriate quantity of water-for-injection to obtain a solution;
  b) addition of pharmaceutically acceptable excipients and a buffering agent to the solution of the polymer in water;

iii) Mixing the solution of step ii b) with a diluting fluid to get a clear solution;

iv) Utilization of a needle having an internal diameter of between 0.305 to 0.356 mm, for addition of a smaller volume of solution of step i) to the solution of step iii); or v) Utilization of a needle having an internal diameter of between 0.559 to 0.711 mm, for addition of a larger volume of the solution of step i) to the solution of step iii);

vi) Injection of the solution of step i) to the solution of step iii), wherein the needle of the syringe through which the solution of step 1) is added shall remain dipped in the solution of step iii); and vii) Optionally, keeping the container containing the solution of step iii) in an inverted position during injection of the solution of step i), so as to completely entrap the poorly water-soluble drug or compound completely or near-completely within the polymeric shell and to produce nanoparticles of the drug or compound having a particle size of 30 to 150 nm. Such a perfusion fluid remains stable for more than 24 hours with more 95% drug remaining loaded in the polymeric micelles.

It should be noted herein that the selection of the diluting fluid, largely depends on the nature of the poorly water-soluble drug or compound utilized as well as on the disorder for which the pharmaceutical composition is administrated. Suitable diluting fluids may be selected from, but not limited to water, saline, dextrose 5% and 10% solutions, dextrose and sodium chloride solution, sodium lactate solution, lactated Ringer solution, mannitol solution, mannitol with dextrose or sodium chloride solution, Ringer's solution, sodium chloride solution, sterile water for injection and multiple electrolyte solutions comprising varying combinations of electrolytes, dextrose, fructose and invert sugar. Preferably, the diluting fluid is a fluid comprising dextrose and water and more preferably dextrose 5% and 10% solutions.

Figure 11:
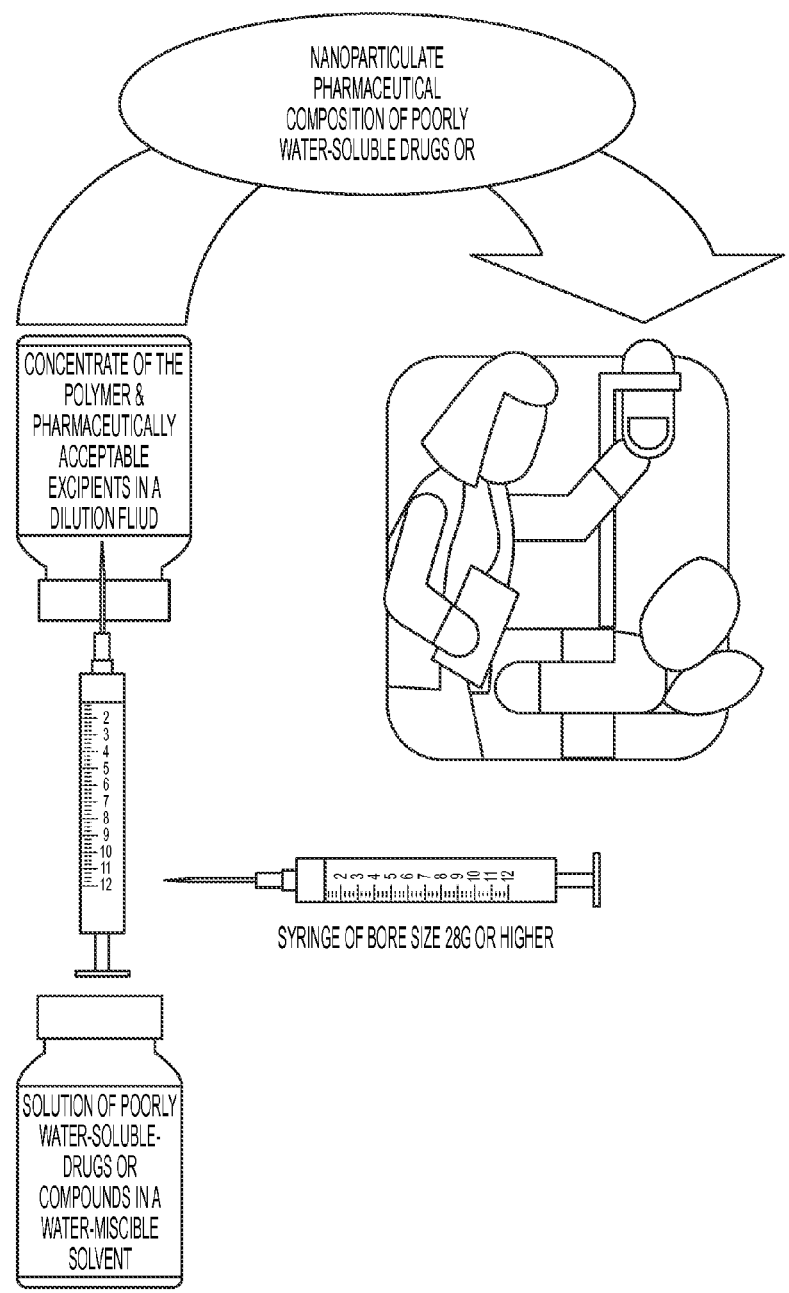
FIG. 11: A Representation of a typical method for preparation and administration to patients in need thereof of the Nan particulate Pharmaceutical Composition of the present invention.

The preferred method for preparation of the nanoparticulate pharmaceutical composition of the present invention and its administration to patients in need thereof is graphically represented in FIG. 11.

The invention is further described in detail with respect to the following non-limiting examples, which, however, should in no way be construed as limiting the scope of the invention.

It should be noted that in the Examples set forth hereinbelow, the diafiltration equipment utilized for purification of the polymer was a Proflux M12 diafiltration device (Make: Millipore) and the dialysis equipment used for purification of the polymer was of Cellulose membrane—D-9402 (Make: Sigma)

Experimental Section

Reference Example-1

Preparation of the Polymer Using the Dialysis Method

The polymerization reaction was carried out in a 2 L glass vessel. 24 g of N-Isopropyl acrylamide, 12 ml of distilled 1-Vinyl-2-pyrrolidone and 4 g of Polyethylene glycol (mol. wt 6000) ester of Maleic anhydride (MPEG) were added to about 2 L of water. To this 11.2 ml of aqueous N,N'-Methylenebisacrylamide (MBA) solution [49 mg/ml] and 8 ml of Tetramethylethylenediamine (d=0.77 gm/ml) were added. The solution was de-aerated by bubbling nitrogen gas for 30 minutes. Then 8 ml of aqueous Ferrous ammonium Sulphate (0.5% w/v) and 12 ml of aqueous Ammonium Persulphate (80% w/v) were added and the reaction was continued for 3 hours with continuous nitrogen bubbling. Polymerization was carried out at 34° C. in a water bath with shaking at 80 rpm.

The solution was filled in dialysis bags and was descended in water (dialysis medium). Dialysis was carried out for 24 hours changing water once. After 24 hours, the solution was removed from the dialysis bags and lyophilized in round bottom flasks.

The detection and quantification of the residual monomers, especially residual VP and NIPAM in the polymer were carried out by Agilent 1100 series HPLC system, using Reverse Phase RP-18 (C-18) columns [Lichrospher RP-18e, 5μ, 250 mm×4 mm]. The Mobile Phase used was a mixture of water and acetonitrile in a ratio of 80:20, at a flow rate of 1 ml/min, with a sample injection volume was 50 μl. The run time was 10 mins and the column temperature was 30° C. and the Detector wavelength was 226 nm. Under the above conditions, NIPAM had a retention time of about 3 minutes, whereas VP had a retention time of about 5 minutes.

Analytical Data: % Residual Monomers i) NIPAM=0.066% (660 ppm) and ii) VP=0.011% (110 ppm).

Example-1

Preparation of the Polymer Using the Diafiltration Method

The polymerization reaction is carried out in two 5 L glass vessels for a batch size of 160 g (4 L×2) of the polymer. To each vessel, 48 g of N-Isopropylacrylamide, 23 ml of distilled 1-Vinyl-2-pyrrolidone and 8 g of Polyethylene glycol (mol. wt 6000) ester of Maleic anhydride (MPEG) were added to about 4 L of water. To this 22.4 nil of aqueous N,N'-Methylenebisacrylamide (MBA) solution [49 mg/ml] and 16 ml of Tetramethylethylenediamine were added. The solution was de-aerated by bubbling nitrogen gas for 30 minutes. Then 16 ml of aqueous Ferrous ammonium Sulphate (0.5% w/v) and 24 nil of aqueous Ammonium Persulphate (80% w/v) were added and the reaction was continued for 3 hours with continuous nitrogen bubbling. Polymerization was carried out at 34° C. in a water bath with shaking at 80 rpm. During polymerization, samples were withdrawn at appropriate time points (0, 15, 60 and 180 minutes) for reaction monitoring.

After polymerization was complete, the solution was filtered through pre-sterilized, disposable 0.2 μm Polyethersulphone membrane 1" capsule filters of 0.8 and 0.2 μm pore size; Type DPS-5101AA-201, mfg by Advanced Microdevices Pvt. Ltd, India). The filtered contents of both the reaction vessels were pooled and subjected to tangential flow filtration using ProfluX M12 (Millipore) diafiltration device to remove residual monomers and other low molecular weight impurities. The combined lot of 8 L of the reaction mixture was initially concentrated to around 2.2 L through diafiltration and then the resultant concentrate is diafiltered using around 30 L of highly purified water. During diafiltration, the reaction mixture is concentrated to around 1 L. Total processing time for the diafiltration for a batch size of 160 g (8 L) is around 4-6 hours. Diafiltered solution is then subjected to lyophilization.

The detection and quantification of the residual monomers, especially residual VP and NIPAM in the polymer were carried out by Agilent 1100 series HPLC system, using Reverse Phase RP-18 (C-18) columns [Lichrospher RP-18e, 5μ, 250 mm×4 mm]. The Mobile Phase used was a mixture of water and acetonitrile in a ratio of 80:20, at a flow rate of 1 ml/min, with a sample injection volume was 50 l. The run time was 10 mins and the column temperature was 30° C. and the Detector wavelength was 226 nm. Under the above conditions, NIPAM had a retention time of about 3 minutes, whereas VP had a retention time of about 5 minutes.

Analytical Data: % Residual Monomers i) NIPAM=<0.001% (<10 ppm) and ii) VP=<0.001% (<10 ppm)

The polymer had the following spectral characteristics, viz.

$^1$H NMR (300 MHz, Bruker Spectometer, CDCl$_3$, δ ppm): 1.15 (br, —CH(CH$_3$)$_2$); 1.45 (br, —CH$_2$—CH—N(VP-Ring); 1.63 (br, —CH$_2$—CHC(=O)NH); 1.99 (br, —CHC(=O)NH—), CH$_2$ (VP ring), 2.36 (CH$_2$, VP ring), 3.0 (—O—CH$_2$—CH$_2$—), 3.23 (CH$_2$—N—); 3.62-3.66 (Br, CH$_2$, MPEG); 3.72 (NH—CH(CH$_3$)$_2$); 3.97 (Br, CH)

$^{13}$C NMR (300 MHz, Bruker Spectometer, CDCl$_3$, δ ppm): 174 (C=O); 76.6-77.6 (multiplet for CDCl$_3$ and CH for polymer backbone), 70.6 (CH$_2$'s MPEG), 41.6 (CH for isopropyl unit), 31.8 (CH$_2$'s, polymer backbone), 22.6 (CH$_3$'s, isopropyl)

FTIR (KBr Pellet, cm$^{-1}$): 3500 (s, OH); 3296 (s, NH, sec-Amide), 2972-2933 (s, CH, CH$_2$, CH$_3$), 1546 (s, NH bend of Amide II and possibly C=O of free acid, minor), 1387, 1367 (doublet of Isopropyl groups, CH$_3$, deformation), 1172-1129 (m, O—C—O)

Example-2

Preparation of Paclitaxel Nanoparticulate Pharmaceutical Composition (Reconstitution in Small Volume i.e. Up to 40 ml)

A] Preparation of Alcoholic solution of Paclitaxel (20 mg/ml): 200 mg of Paclitaxel was dissolved in 10.0 ml of Ethanol.

B] Preparation of Aqueous Concentrate of Polymer and Excipients: 100 mg of the Polymer obtained by Example-1, 66.7 mg of sodium deoxycholate and 100 mg of sodium citrate were dissolved in 10 ml water to give a clear solution.

C] Preparation of Paclitaxel Nanoparticles (0.6 mg/ml): 1.0 ml of the aqueous concentrate of the polymer and excipients of step B] was dissolved in 31.3 ml of 10% Dextrose solution to obtain a clear solution. 1.0 ml of the alcoholic solution of Paclitaxel of step A] was added to the above solution through needle having an internal diameter of 0.330 mm within 4 seconds to obtain nanoparticles of Paclitaxel at a concentration of 0.6 mg/ml The pharmaceutical composition thus prepared had the following characteristics:

| Dilution Fluid | Polymer Concn. (mg/ml) | Sodium deoxycholate Concn. (mg/ml) | Sodium Citrate Concn. (mg/ml) | Paclitaxel Concn. (mg/ml) | Particle Size (nm) | Stability |
|---|---|---|---|---|---|---|
| 10% Dextrose | 0.3 | 0.2 | 0.3 | 0.6 | ≈80 | >24 hrs |

Example-3

Preparation of Paclitaxel Nanoparticulate Pharmaceutical Composition (Reconstitution in Large Volume i.e. Up to 500 ml)

A] Preparation of Alcoholic solution of Paclitaxel (20 mg/ml): 400 mg of Paclitaxel was dissolved in 20.0 ml of Ethanol.

B] Preparation of Aqueous Concentrate of Polymer and Excipients: 200 mg of the Polymer obtained by Example-1, 133.4 mg of sodium deoxycholate and 200 mg of sodium citrate were dissolved in 20 ml water to give a clear solution.

C] Preparation of Paclitaxel Nanoparticles (0.6 mg/ml): 15.0 ml of the aqueous concentrate of the polymer and excipients of step B] was dissolved in 500 ml of 10% Dextrose solution to obtain a clear solution. 15.0 ml of the alcoholic solution of Paclitaxel of step A] was added to the above solution through a needle having an internal diameter of 0.711 mm within 8 seconds to obtain nanoparticles of Paclitaxel at a concentration of 0.6 mg/ml The pharmaceutical composition thus prepared had the following characteristics:

| Dilution Fluid | Polymer Concn. (mg/ml) | Sodium deoxycholate Concn. (mg/ml) | Sodium Citrate Concn. (mg/ml) | Paclitaxel Concn. (mg/ml) | Particle Size (nm) | Stability |
|---|---|---|---|---|---|---|
| 10% Dextrose | 0.3 | 0.2 | 0.3 | 0.6 | ≈85 | >24 hrs |

Example-4

Preparation of Nanoparticulate Pharmaceutical Composition of a Betulinic Acid Derivative [MJ-1098 of Formula (II)]

A] Preparation of a solution of MJ-1098 (15 mg/ml): MJ-1098 (15 mg) was dissolved in a mixture of 0.15 ml of N,N-Dimethylacetamide, 0.01 ml of Polysorbate 80 and 0.84 ml of Ethanol was added to the above solution and dissolved by sonication.

B] Preparation of Aqueous Concentrate of Polymer and Excipients: 10 mg of the Polymer obtained by Example-1, 6.67 mg of sodium deoxycholate and 10 mg of sodium citrate were dissolved in 1 ml water to give a clear solution.

C] Preparation of MJ-1098 Nanoparticles (0.75 mg/ml): 0.3 ml of the aqueous concentrate of the polymer and excipients of step B] was dissolved in 9.2 ml of 5% Dextrose solution to obtain a clear solution. 0.5 ml of the solution of MJ-1098 of step A] was added to the above solution through a needle having an internal diameter of 0.330 mm within 3 seconds to obtain nanoparticles of MJ-1098 at a concentration of 0.75 mg/ml The pharmaceutical composition thus prepared had the following characteristics:

| Dilution Fluid | Polymer Concn. (mg/ml) | Sodium deoxycholate Concn. (mg/ml) | Sodium Citrate Concn. (mg/ml) | Mj-1098 Concn. (mg/ml) | Particle Size (nm) | Stability |
|---|---|---|---|---|---|---|
| 5% Dextrose | 0.3 | 0.2 | 0.3 | 0.75 | ≈62 | >24 hrs |

Example-5

Preparation of Nanoparticulate Pharmaceutical Composition of a Betulinic Acid Derivative [DRF-4012 of Formula (III)]

A] Preparation of a solution of DRF-4012 (20 mg/ml): MJ-DRF-4012 (20 mg) was dissolved in a mixture of 0.01 ml of Polysorbate 80 and 0.99 ml of Ethanol and dissolved by sonication.

B] Preparation of Aqueous Concentrate of Polymer and Excipients: 10 mg of the Polymer obtained by Example-1, 6.67 mg of sodium deoxycholate and 10 mg of sodium citrate were dissolved in 1 ml water to give a clear solution.

C] Preparation of DRF-4012 Nanoparticles (0.60 mg/ml): 0.33 ml of the aqueous concentrate of the polymer and excipients of step B] was dissolved in 10.44 ml of 5% Dextrose solution to obtain a clear solution. 0.33 ml of the solution of DRF-4012 of step A] was added to the above solution through a needle having an internal diameter of 0.305 mm within 3 seconds to obtain nanoparticles of DRF-4012 at a concentration of 0.6 mg/ml The pharmaceutical composition thus prepared had the following characteristics:

| Dilution Fluid | Polymer Concn. (mg/ml) | Sodium deoxycholate Concn. (mg/ml) | Sodium Citrate Concn. (mg/ml) | DRF-4012 Concn. (mg/ml) | Particle Size (nm) | Stability |
|---|---|---|---|---|---|---|
| 5% Dextrose | 0.3 | 0.2 | 0.3 | 0.6 | ≈70 | >24 hrs |

Example-6

Preparation of Nanoparticulate Pharmaceutical Composition of a Betulinic Acid Derivative [DRF-4015 of Formula (IV)]

A] Preparation of a solution of DRF-4015 (20 mg/ml): MJ-DRF-4015 (20 mg) was dissolved in a mixture of 0.01 ml of Polysorbate 80 and 0.99 ml of Ethanol and dissolved by sonication.

B] Preparation of Aqueous Concentrate of Polymer and Excipients: 10 mg of the Polymer obtained by Example-1, 6.67 mg of sodium deoxycholate and 10 mg of sodium citrate were dissolved in 1 ml water to give a clear solution.

C] Preparation of DRF-4015 Nanoparticles (0.60 mg/ml): 0.33 ml of the aqueous concentrate of the polymer and excipients of step B] was dissolved in 10.44 ml of 5% Dextrose solution to obtain a clear solution. 0.33 ml of the solution of DRF-4015 of step A] was added to the above solution through a needle having an internal diameter of 0.330 mm within 4 seconds to obtain nanoparticles of DRF-4015 at a concentration of 0.6 mg/ml The pharmaceutical composition thus prepared had the following characteristics:

| Dilution Fluid | Polymer Concn. (mg/ml) | Sodium deoxycholate Concn. (mg/ml) | Sodium Citrate Concn. (mg/ml) | DRF-4015 Concn. (mg/ml) | Particle Size (nm) | Stability |
|---|---|---|---|---|---|---|
| 5% Dextrose | 0.3 | 0.2 | 0.3 | 0.6 | ≈46 | >24 hrs |

Example-7

Preparation of Docetaxel Nanoparticulate Pharmaceutical Composition

A] Preparation of Alcoholic solution of Docetaxel (40 mg/ml): 200 mg of Docetaxel was dissolved in 5.0 ml of Ethanol.

B] Preparation of Aqueous Concentrate of Polymer and Excipients: 400 mg of the Polymer obtained by Example-1, 400 mg of sodium deoxycholate and 400 mg of sodium citrate were dissolved in 10 ml water to give a clear solution.

C] Preparation of Docetaxel Nanoparticles (0.5 mg/ml): 4.0 ml of the aqueous concentrate of the polymer and excipients of step B] was dissolved in 35.5 ml of 10% Dextrose solution to obtain a clear solution. 0.5 ml of the alcoholic solution of Docetaxel of step A] was added to the above solution through a needle having an internal diameter of 0.330 mm within 3 seconds to obtain nanoparticles of Docetaxel at a concentration of 0.5 mg/ml The pharmaceutical composition thus prepared had the following characteristics:

| Dilution Fluid | Polymer Concn. (mg/ml) | Sodium deoxycholate Concn. (mg/ml) | Sodium Citrate Concn. (mg/ml) | Docetaxel Concn. (mg/ml) | Particle Size (nm) | Stability |
|---|---|---|---|---|---|---|
| 10% Dextrose | 4.0 | 4.0 | 4.0 | 0.5 | ≈125 | >24 hrs |

Example-8

Preparation of Etoposide Nanoparticulate Pharmaceutical Composition

A] Preparation of a solution of Etoposide (20 mg/ml): 20 mg of Etoposide was dissolved in a mixture of 0.10 ml of N,N-dimethyl acetamide and 0.90 ml of Ethanol under sonication.

B] Preparation of Aqueous Concentrate of Polymer and Excipients: 10 mg of the Polymer obtained by Example-1, 6.67 mg of sodium deoxycholate and 10 mg of sodium citrate were dissolved in 10 ml water to give a clear solution.

C] Preparation of Etoposide Nanoparticles (0.6 mg/ml): 0.3 ml of the aqueous concentrate of the polymer and excipients of step B] was dissolved in 9.4 ml of 5% Dextrose solution to obtain a clear solution. 0.3 ml of the alcoholic solution of Etoposide of step A] was added to the above solution through a needle having an internal diameter of 0.330 mm within 3 seconds to obtain nanoparticles of Etoposide at a concentration of 0.6 mg/ml The pharmaceutical composition thus prepared had the following characteristics:

| Dilution Fluid | Polymer Concn. (mg/ml) | Sodium deoxycholate Concn. (mg/ml) | Sodium Citrate Concn. (mg/ml) | Etoposide Concn. (mg/ml) | Particle Size (nm) | Stability |
|---|---|---|---|---|---|---|
| 5% Dextrose | 0.3 | 0.2 | 0.3 | 0.6 | ≈50 | >24 hrs |

Example-9

Determination of Pharmacokinetics, Biodistribution, and Elimination of [$^{14}$C] Labelled Polymer in Mice 30 male Swiss albino mice, 6-8 weeks of age, weighing approximately 25-30 gms, were randomly divided into five groups consisting of six animals each. [$^{14}$C]-labelled polymer was diluted in deionised water to 5 mg/ml based on the specific activity of the polymer. All animals received a single dose of [$^{14}$C] polymer 40 mg/kg by intravenous injection.

In the pharmacokinetics study 100 µl of blood was collected from the animals by retro-orbital bleeding under anesthesia at time points of 3, 10, 30 min, 1, 2, 4, 8, 16, and 24 hrs post administration into EDTA containing tubes. For excretion studies, urine and feaces was collected from the metabolic cage or by force (10 minutes). At termination (10 min, 60 min, 24 and 48 hrs) adrenal, brain, lungs, liver, heart, kidneys, spleen, stomach, small intestine, large intestine, feaces, urine, urinary bladder, eye, skin, skin, thigh muscle, testing and epididymis were collected, rinsed, excised and weighed:

The concentrations of the [$^{14}$C] polymer in blood and urine were determined by combining 50 µl of blood/urine with 5 ml of liquid scintillation cocktail. Faeces and tissues (not more than 0.5 gms) were homogenized in deionised water to obtain 20% homogenate before combining 500 µl with 5 ml of liquid scintillation cocktail. Samples were analysed by liquid scintillation analyser. The counts per minute (CPM) were converted to amount of the [$^{14}$C] polymer in mg/ml based on linearity and Quenching curves.

The radioactive blood concentration profile revealed a biphasic curve with short elimination half-life $T_{1/2}$ (β) of 0.448±0.157 hours (26.88 min) and rapid clearance of 54.7 ml/hr.

The dominant route of elimination was found to be urine (urine, 66.91% vs feaces, 17.39% at 48 hrs) and recovery data collected up to 48 hrs accounts for 84.87% of radioactivity injected. Tissue distribution was negligible. The kidney, liver, skin and intestine were found to be the target organs. However, the level of the polymer in tissues was rapidly cleared via urine and faeces.

Tissue distribution was negligible in kidney, liver, skin and intestine presenting with the highest levels of radioactivity. However, levels of polymer in tissues were rapidly cleared via urine and feaces.

In conclusion, the study shows that the polymer is rapidly eliminated from the body without being deposited in vital organs. Although, the polymer is known to be non-biodegradable, the rapid and efficient clearance primarily via urine suggests the safety and utility of the polymer for human use.

Example-10

Determination of the Possible Local Toxicity, if any, at the Site of Administration Upon Five Day Intravenous Bolus Administration of 125 mg/kg of the Polymer in Rabbits The test substance dissolved in dextrose 10% at a concentration of 75 mg/ml was administered intravenously with a 5 ml disposable syringe and 23G needle into the marginal vein of the right ear of each rabbit at 125 mg/kg daily for five consecutive days. Left ear served, as control and received 10% Dextrose by the same route. Dosing volume was adjusted to not more than 3.5 ml/Kg. Body weight of animal. Periodic observations for local toxicity were made at the site of injection at 5 min, 10 min, 30 min, 60 min and 24 hrs on each day for days 1 to 5. Punch biopsies at site of injection were taken from both ears of all six rabbits on Day 7.

A five day continuous intravenous administration of 75 mg/ml of the polymer at a dose of 125 mg/kg in rabbit ear vein causes mild to moderate thrombophlebitis at the site of injection of 10% Dextrose injected rabbits. It may be concluded that the dose of the polymer selected does not cause any local toxicity at the site of administration.

Example-11

Determination of the Possible Target Organ(s) of Toxicity with Special Reference to Microvasculature Upon Five Days Intravenous Bolous Administration of 400 mg/kg of the Polymer in Wistar Rats The test substance was dissolved in Dextrose 10% and administered intravenously with the help of a 5 ml disposable syringe and 23 G needle into the tail vein of each rat at 400 mg/kg. Control animals received 05 Dextrose only by the same route. Dosing volume was adjusted to 5 ml/kg body weight of the animals. Periodic observations (Day 7, 14 and 21 post-treatment) on adverse effects (general examination and laboratory parameters) and deaths were recorded. All the animals were sacrificed and necropsied.

Under the conditions of study, five-day intravenous bolus administration of the polymer at a dose level of 400 mg/kg body weight does not produce any mortality or any physical toxic signs or symptoms in treated rats.

Individual and mean body weights of rats showed a steady increase in both the polymer treated and control groups. No significant difference was noted for body weight for treated animals as compared to that of the control.

In rats treated with the polymer, haematological parameters were within normal limits throughout the study. Significant differences were detected at base line for total bilirubin (p=0.0471) and Uric acid (p=0.0157) for interim group and total protein (p=0.0005) and Uric acid (p=0.0404) for terminal group animals over the control animals. However, all values are within the normal limits.

The photoactometer test showed that there was no significant difference between the locomotor activity between the control and treated groups on day 7 and 21 respectively suggesting that the polymer does not have any neurotoxicity.

The treated and control groups specimens showed similar histological features. All organs studied showed normal structure on light microscopic examination. The microvasculature in each organ was carefully examined and no pathological features were seen in any of the organs. Further, there were no changes in microvasculature of the polymer treated animals.

From the above observations, it was seen that the polymer at a dose of 400 mg/kg body weight administered for five consecutive days did not cause any general toxicity or any significant haematological toxicity. However, total bilirubin was found to be significantly higher for the terminal group as compared top the control group on Day 21.

Example-12

Determination of the Possible Target Organ(s) of Toxicity with Special References to Microvasculature Upon Single Intravenous Bolus Administration of 800 mg/kg of the Polymer in Wistar Rats The test substance dissolved in dextrose 10% was dissolved in Dextrose 10% was administered with the help of a 1 ml disposable syringe and 26 G needle into the tail vein of each rat at 800 mg/kg. Control animals received 10% dextrose only by the same route. Dosing volume was adjusted to 5 ml/kg body weight of the animals. Periodic observations (Day 1, 3 and 7 post-treatment) on adverse effects (general examination and laboratory parameters) and deaths were recorded. All the animals were sacrificed and necropsied.

Under the conditions of the study, single intravenous bolus administration of the polymer at a dose level of 800 mg/kg Body weight does not produce any mortality or any observable toxic signs or symptoms in rats.

Individual and mean body weights of rats show a steady increase in both the polymer treated and control groups. In rats treated with the polymer, haematological parameters were within normal limits throughout the study. In rats treated with the polymer, biochemical parameters were within normal limits throughout the study. The histopathological studies show that there is no significant difference between control and treated groups of rats. Photomicrographs of the polymer treated rats sacrificed on Day 3 and Day 7 post injection show that there are no apparent microvasculature changes in all four organs examined (Brain, Eye, Kidney and Skin)

From the above observations it is seen that the polymer at a dose of 800 mg/kg body weight does not cause any general toxicity or any significant haematological and biochemical toxicity or changes in microvasculature and can be considered to be safe when administered intravenously in rats.

Example-13

Determination of the Possible Local Toxicity, if any, at the Site of Administration (Subcutaneous) of the Polymer in Rabbits A single injection of 0.1 ml of the test substance dissolved in dextrose 10% at a concentration of 75 mg/ml was administered subcutaneously with 1 ml disposable syringe and 23 G needle into the right ear lobe of each of the six rabbits. Control will receive 0.1 ml of 10% dextrose by the same route in the left ear lobe of all six rabbits. Periodic observations for local toxicity were made at the site of injection at 5 min, 10 min, 30 min, 60 min and 24 hrs.

A single sub cutaneous administration of 100 µl of 75 mg/ml of the polymer or 100 µl of Dextrose in the rabbit ear causes mild inflammation at the site of injection when tested after 48 hrs post injection. It may be concluded that the polymer selected does not cause any local toxicity at the site of administration following sub-cutaneous administration

Example-14

Determination of Six Months Dose Toxicity Study by Intravenous Route of the Polymer in Rats The polymer used in nanoparticle formulation was administered at dose level equivalent to 10 mg/kg of drug. Controls were administered Dextrose (10%) intravenously in the lateral tail vein cyclically once every three weeks for a period of 180 Days (approximately 26 weeks). Observations comprised of mortality, clinical signs, body weight, food and water consumption, clinical laboratory investigations, organ weights and histopathology.

Animals of treated and control groups remained generally active and healthy during the period of study. There was no treatment related mortality except few incidental deaths due to infections in both treatment and control groups. Animals of both sexes showed a progressive increase in body weight and there were no changes in feed or water consumption during the study. Haematology parameters in both males and females were within the normal range as reported for Wistar rats. However, in the treatment group, there was minor decrease, yet within normal limits, of WBC and neutrophile counts in males and Neutrophile count in females. A mild increase in Reticulocyte count was noticed in both treated and control group.

Blood biochemistry parameters in both males and females were within the normal range as reported for Wistar rats. Minor Changes included slightly higher than normal values in Glucose, ALP and Creatinine in both males and females of treated and control groups. Mild increase in Triglycerides of treatment group males was seen at 6 months. Urine parameters in both males and females were within normal limits.

The invention claimed is:

1. A process for preparation of a polymer of high purity and substantially free of respective toxic monomeric contaminants and containing respective toxic monomeric contaminants in amounts less than 0.001%, comprising the steps of:
   i) Dissolving N-isopropylacrylamide (NIPAM), 1-vinylpyrrolidone (VP), and ester of maleic anhydride and polyethylene glycol (MPEG) in water;
   ii) Adding in succession to the solution of step i), a cross-linking agent and an activator;
   iii) Bubbling an inert gas into the solution of step ii) for a period of between 30 to 60 minutes;
   iv) Adding an activator and a polymerization initiator to the solution of step iv);
   v) Polymerizing the solution of step iv), at a temperature of between 25° C. to 45° C., under an atmosphere of an inert gas for 3 to 6 hours;
   vi) Subjecting the solution of step v) to filtration through pre-sterilized filters and collecting the filtrate;
   vii) Subjecting the filtrate of step vi) to diafiltration and collecting the filtrate;
   viii) Optionally subjecting the filtrate of step vii) to an additional step of diafiltration and collecting the filtrate; and
   ix) Optionally subjecting the filtrate of step vii) or viii) to lyophilization to obtain a lyophilized powder of the polymer.

2. The process according to claim 1, wherein the weight ratio of the monomers, NIPAM:VP is in the range of between 55:22 to 65:35, and the weight ratio of monomers, (NIPAM+VP):MPEG is in the range of between 90:10 to 95:5.

3. The process according to claim 1, wherein the weight ratio of the monomers, NIPAM:VP is in the range of between 58:32 to 62:28, and the weight ratio of monomers, (NIPAM+VP):MPEG is in the range of between 80:20 to 95:5.

4. The process according to claim 1, wherein the cross-linking agent is a bi-functional vinyl derivative.

5. The process according to claim 4, wherein the bi-functional vinyl derivative is N,N$^1$-methylene bis acrylamide.

6. The process according to claim 1, wherein the cross-linking agent is employed in the range of between 1.3 to 1.5% w/w of the total monomer content.

7. The process according to claim 6, wherein the cross-linking agent is employed in the range of between 1.35 to 1.4% w/w of the total monomer content.

8. The process according to claim 1, wherein the activator is selected from any one of Tetramethylethylene diamine or Ferrous Ammonium Sulphate, or a combination of both.

9. The process according to claim 1, wherein the activator is employed in quantities in the range of between 15 to 18% w/w of the total monomer content.

10. The process according to claim 9, wherein the activator is employed in quantities in the range of between 15 to 16% w/w of the total monomer content.

11. The process according to claim 1, wherein the polymerization initiator is selected from peroxide polymerization initiators, nitrile polymerization initiators, or inorganic salt based polymerization initiators.

12. The process according to claim 11, wherein the polymerization initiator is Ammonium perdisulphate or Ammonium persulphate.

13. The process according to claim 1, wherein the polymerization initiator is employed in the range of between 20 to 30% w/w of the total monomer content.

14. The process according to claim 13, wherein the polymerization initiator is employed in the range of between 23 to 25% w/w of the total monomer content.

15. The process according to claim 1, wherein the inert gas is argon or nitrogen.

16. The process according to claim 1, wherein the pre-sterilized filter utilized in step v) is a disposable 0.21 μm Polyethersulphone membrane 1-inch capsule filter having a pore size of 0.8 and 0.2 μm.

17. The process according to claim 1, wherein the diafiltration equipment utilized in steps vi) and vii) is a Millipore Proflux M12 diafiltration device.

* * * * *

UNITED STATES PATENT AND TRADEMARK OFFICE
CERTIFICATE OF CORRECTION

PATENT NO. : 8,927,023 B2  
APPLICATION NO. : 13/633638  
DATED : January 6, 2015  
INVENTOR(S) : Burman et al.

Page 1 of 1

It is certified that error appears in the above-identified patent and that said Letters Patent is hereby corrected as shown below:

On the title page item (57), in "Abstract", in column 2, line 3, delete "1-Vinylpyrrolidne" and insert --1-Vinylpyrrolidone--, therefor On the title page item (57), in "Abstract", in column 2, line 4, delete "N-Isopropylactylamide" and insert --N-Isopropylacrylamide--, therefor In the claims In column 46, line 38, in Claim 16, delete "0.21" and insert --0.2--, therefor Signed and Sealed this  
Twenty-eighth Day of April, 2015

Michelle K. Lee  
*Director of the United States Patent and Trademark Office*